US009212134B2

(12) United States Patent
Basu et al.

(10) Patent No.: US 9,212,134 B2
(45) Date of Patent: Dec. 15, 2015

(54) INHIBITORS OF VIRAL ENTRY INTO MAMMALIAN CELLS

(75) Inventors: Arnab Basu, Acton, MA (US); Debra M. Mills, Ayer, MA (US); John D. Williams, Watertown, MA (US); Bing Li, Northborough, MA (US); Norton P. Peet, North Andover, MA (US); Terry L. Bowlin, Maineville, OH (US)

(73) Assignee: Microbiotix, Inc., Worcester, MA (US)

( * ) Notice: Subject to any disclaimer, the term of this patent is extended or adjusted under 35 U.S.C. 154(b) by 93 days.

(21) Appl. No.: 13/821,682

(22) PCT Filed: Sep. 13, 2011

(86) PCT No.: PCT/US2011/051389

§ 371 (c)(1), (2), (4) Date: Aug. 15, 2013

(87) PCT Pub. No.: WO2012/037119
PCT Pub. Date: Mar. 22, 2012

(65) Prior Publication Data

US 2013/0331456 A1 Dec. 12, 2013

Related U.S. Application Data

(60) Provisional application No. 61/382,215, filed on Sep. 13, 2010.

(51) Int. Cl.

| | |
|---|---|
| *C07C 311/44* | (2006.01) |
| *C07C 311/32* | (2006.01) |
| *A61K 31/18* | (2006.01) |
| *A61P 31/16* | (2006.01) |

(52) U.S. Cl.
CPC ............... *C07C 311/44* (2013.01); *A61K 31/18* (2013.01)

(58) Field of Classification Search
CPC ..... C07C 311/32; C07C 311/44; A61K 31/18
USPC ............... 514/604, 605, 601, 602; 564/92, 99
See application file for complete search history.

(56) References Cited

U.S. PATENT DOCUMENTS

| | | | | |
|---|---|---|---|---|
| 2004/0034232 | A1 | 2/2004 | Kontani et al. | |
| 2009/0088420 | A1 | 4/2009 | Neamati et al. | |
| 2009/0137545 | A1 | 5/2009 | Kauffmann-Hefner et al. | |
| 2010/0216852 | A1 | 8/2010 | Ausubel et al. | |
| 2012/0189614 | A1* | 7/2012 | Basu et al. | 424/130.1 |

FOREIGN PATENT DOCUMENTS

| | | | |
|---|---|---|---|
| CN | 1473157 | A | 2/2004 |
| CN | 101108191 | | 1/2008 |
| EP | 1340750 | A1 | 9/2009 |
| WO | WO9947529 | A1 | 9/1999 |
| WO | WO2004019941 | A1 | 3/2004 |
| WO | WO2008022945 | A1 | 2/2008 |
| WO | WO2010111713 | A2 | 9/2010 |
| WO | WO2011046646 | A2 | 4/2011 |
| WO | WO2012017166 | A2 | 2/2012 |

OTHER PUBLICATIONS

Virgin et al. Cell 2009, 138 (1), 30-50.*
Noueiry et al., "Identification of Novel Small-Molecule Inhibitors of West Nile Virus Infection", J. of Virol., 81(21): 11992-12004 (2007).
Severson et al., "High-Throughput Screening of a 100,000-Compound Library for Inhibitors of Influenza a Virus (H3N2)", J. of Biomolecular Screening, 13(9): 879-887 (2008).
Basu et al., "New Small Molecule Entry Inhibitors Targeting Hemagglutinin-Mediated Influenza A Virus Fusion", J. Virology, 88(3): 1447-1460 (2014).
Stevens et al., "Structure and Receptor Specificity of the Hemagglutinin from an H5N1 Influenza Virus", Science, 312: 404-410 (2006).

* cited by examiner

*Primary Examiner* — Sreeni Padmanabhan
*Assistant Examiner* — Irina Neagu
(74) *Attorney, Agent, or Firm* — Leon R. Yankwich; David G. O'Brien; Yankwich & Associates, P.C.

(57) ABSTRACT

The present invention is related to the development of compounds and methods for inhibiting viral infection in a mammal. A pseudotype virus was developed for use in a high throughput assay for identifying nonpeptidic small molecule inhibitors that prevent viral entry into a host cell.

11 Claims, 10 Drawing Sheets

```
┌─────────────────────────────────────────────────┐
│ HTS ASSAY USING HIV/HA(H5) TO SCREEN FOR ENTRY INHIBITORS │
└─────────────────────────────────────────────────┘
                          │
      <90% INHIBITION ↓         ↓ >90% INHIBITION
   ┌──────────────────┐   ┌──────────────────────────────┐
   │ NO FURTHER INTEREST │   │ TEST FOR HA SPECIFICITY USING HIV/VSV-G │
   └──────────────────┘   └──────────────────────────────┘
             ↑ NON-SPECIFIC        │
             │         ┌───────────────────────────────────┐
             │         │ RECONFIRMATION OF HITS BY HIV/HA(H5) │
             │         │ WITH REORDERED COMPOUNDS           │
             │         └───────────────────────────────────┘
             │  NOT CONFIRMED       │
             │                      ↓
             │              ┌──────────────────┐
             │              │ TEST FOR CYTOTOXICITY │
             │              └──────────────────┘
             │  CYTOTOXIC (CC₅₀ <25μM)    NON-CYTOTOXIC (CC₅₀ >25μM)
             │                      ↓
             │     ┌─────────────────────────────────────────┐
             │     │ SCREENING OF HITS AGAINST INFECTIOUS INFLUENZA │
             │     └─────────────────────────────────────────┘
             │   IC₅₀ >25μM          IC₅₀ <25μM
             │                      ↓
             │            ┌───────────────────────────────┐
             │            │ HA SPECIFIC INFLUENZA INHIBITORS │
             │            └───────────────────────────────┘
```

Fig. 11

INHIBITORS OF VIRAL ENTRY INTO MAMMALIAN CELLS

CROSS-REFERENCE TO RELATED APPLICATIONS

This application is a United States national stage filing under 35 U.S.C. §371 of international (PCT) application no. PCT/US2011/051389, filed Sep. 13, 2011, and designating the US, which claims priority to U.S. Provisional Appln. No. 61/382,215 filed Sep. 13, 2010.

STATEMENT REGARDING FEDERALLY SPONSORED RESEARCH

This invention was made with government support under grant AI072861 awarded by the National Institutes of Health. The government has certain rights in the invention.

FIELD OF THE INVENTION

The present invention is directed to the discovery of novel nonpeptidic small molecules that function as inhibitors of viral entry into a host cell by targeting protein present on the surface of the virus. In particular, the present invention is directed to the discovery of anti-H5N1 entry inhibitors that specifically target the hemagglutinin (HA) envelope glycoprotein, which mediates influenza virus entry through receptor binding and fusion of the virus with host cells, and to inhibitors that target ebola virus surface proteins and prevent entry of ebola virus into a host cell.

BACKGROUND OF THE INVENTION

Viruses are by far the most abundant parasites on earth, and they have been found to infect all types of cellular life including animals, plants, and bacteria. However, different types of viruses can infect only a limited range of hosts and many are species-specific. Some, such as smallpox virus for example, can infect only one species—in this case humans, and are said to have a narrow host range. Other viruses, such as rabies virus, can infect different species of mammals and are said to have a broad range. The viruses that infect plants are harmless to animals, and most viruses that infect other animals are harmless to humans. Examples of common human diseases caused by viruses include the common cold, influenza, chickenpox and cold sores. Many serious diseases such as ebola, AIDS, avian influenza and SARS are caused by viruses. The relative ability of viruses to cause disease is described in terms of virulence. A pandemic is a worldwide epidemic. The 1918 flu pandemic, for example, commonly referred to as the Spanish flu, was a category 5 influenza pandemic caused by an unusually severe and deadly influenza A virus. The victims were often healthy young adults, in contrast to most influenza outbreaks, which predominantly affect juvenile, elderly, or otherwise-weakened patients. Other examples of viruses capable of causing widespread pandemice include, but are not limited to, avian influenza virus, ebola virus, and vesicular stomatitis virus.

Interfering with virus entry is a novel and attractive therapeutic strategy to control virus infection. Proof of principle of this approach has come from peptidic HIV inhibitor enfuvirtide. While confirming the therapeutic benefit of entry inhibitors for the treatment of viral infections, enfuvirtide has also highlighted potential problems of peptidic antivirals. Large heptad repeat-derived peptides, like enfuvirtide, are costly to manufacture, and poor absorption from the gastrointestinal tract necessitates i.v. delivery.

Influenza Virus

The expanding geographic distribution of the avian influenza A (H5N1) virus has put more humans at risk of infection and absence of pre-existing immunity to these viruses in the human population has raised the concern of a new influenza pandemic. (Trampuz et al., Mayo Clin Proc., 79: 523-530 (2004)). In addition, the virus has crossed the species barrier to cause numerous human fatalities in certain regions of Asia and Europe since 1997. (Beigel et al., 2005 supra). Currently there is no effective vaccine against this virus for humans. (Cox et al., Topley & Wilson's Microbiology and Microbial Infections, Collier L, Balows A, Sussman M., eds., London, pp. 634-698 (2005); Kemble, G., and H. Greenberg, Vaccine, 21: 1789-1795 (2003)).

The family Orthomyxoviridae comprises influenza A, B, and C viruses, and Thogoto- and Isavirus. (Cox et al., 2005, supra; Lamb, R. A., and R. M. Krug, Fields Virology, Fourth ed., vol. 1, pp. 1487-1531, Knipe, D. M., Howley, P. M., eds., Lippincott Williams and Wilkins Publishers, Philadelphia (2001)). Influenza pandemics in humans are caused by influenza A viruses. Influenza A viruses contain 8 single-stranded, negative-sense viral RNAs (vRNAs) that encode 10-11 proteins. (Lamb, R. A., 2001, supra; Wright, P. F., and R. G. Webster, Fields Virology, Fourth ed., vol. 1, p. 1533-1579, Knipe, D. M., Howley, P. M., eds., Lippincott Williams and Wilkins Publishers, Philadelphia (2001)).

Influenza A virus contains two surface glycoproteins, hemagglutinin (HA) and neuraminidase (NA) (FIG. 1). Based on the antigenicity of the HA and NA proteins, 16 different HA subtypes (H1-H16) and 9 different NA subtypes (N-1-N9) of influenza A viruses have been identified. Of these, only a limited number of virus subtypes circulate in humans (i.e., H1-H3, and N1, N2). (Lamb, R. A., 2001, supra; Wright, P. F., 2001, supra).

HA is the major viral antigen and mediates receptor-binding and membrane fusion activities, while NA is a receptor-destroying enzyme which releases the viral particles from the cell surface. (Lamb, R. A., 2001, supra; Wright, P. F., 2001, supra). The prototypic HA is synthesized as a single polypeptide and subsequently cleaved into HA1 and HA2 subunits. HA cleavage is required for infectivity, because it generates the hydrophobic N-terminus of HA2, which mediates fusion between the viral envelope and the cell membrane. (Steinhauer, D. A., Virology, 258: 1-20 (1999); Skehel, J. J. and D. C. Wiley, Annu. Rev. Biochem., 69: 531-569 (2000); Lamb, R. A., 2001, supra; Wright, P. F., 2001, supra).

Several steps in the HA-mediated entry process are attractive targets for new anti-influenza therapeutics:

(a) Attachment of HA to its sialic acid receptors: The receptor-binding site of HA is a pocket located on each subunit at the distal globular part of HA1, and binds to cell surface sialic acid residues in a multivalent attachment process. The residues (Y98, W153, H183, E190, L194) forming the pocket are largely conserved among all subtypes of influenza. (Skehel, J. J., 2000, supra).

Therefore, inhibitors can be developed that will block binding of the virus to cells by either binding to receptor binding sites or preventing the interaction through some other mechanism. Several high molecular weight polymers, such as polyphenol and lignin, have been reported to inhibit binding of the virus to the cell membrane. (Sakagami et al., Sieb. Et Zucc. In Vivo, 6: 491-496 (1992); Mochalova et al., Antiviral Research, 23: 179-190 (1994); Sidwell et al., Chemotherapy, 40: 42-50 (1994)).

(b) HA-mediated virus-cell fusion: Influenza virus enters its host cell by receptor-mediated endocytosis, followed by acid-activated membrane fusion in endosomes. The low pH environment in the endosomes is required to trigger the transition of HA from the non-fusogenic to the fusogenic conformation. This conformational change relocates the fusion peptide segment from the amino-terminus of HA2 to the tip of the molecule. Following this conformational change, the fusion peptides fuse the viral envelope with the endosomal membrane. Inhibition of endosomal H+-ATPase, that blocks the acidification of endosomes, strongly inhibits the replication of influenza virus in MDCK cells. (Hernandez et al., Annu. Rev. Cell Dev. Biol., 12: 627-661 (1996)). However, endosomal H+-ATPase activity is not a virus-specific target and interfering with H+-ATPase activity may lead to undesirable toxic side effects;

(c) The fusogenic trimer-of-hairpins structure: Class I fusion proteins can assume three distinct conformational states, the (i) nonfusogenic native structure, in which the fusion peptide is buried within the trimeric protein; (ii) transient prehairpin intermediate, in which the N-terminal fusion peptide is extended to penetrate the host-cell target membrane; and (iii) fusogenic trimer-of-hairpins structure, in which the C- and N-terminal heptad repeat peptides (HR-C and HR-N) are associated in a six-helix-bundle conformation, is critical for fusion. (Hernandez et al., 1996, supra; Dutch et al., Biosci. Rep., 20: 597-612 (2000); Eckert, D. and Kim P., Annu. Rev. Biochem., 70: 777-810 (2001)). The fusion trimer-of-hairpins structure is maintained through protein-protein interactions. At the C-terminal of the HR-N trimer surface, a deep groove exists that opens into a cavity, forming a hydrophobic pocket recognized as a potential binding site for small molecule inhibitors. Targeting the conserved receptor binding domain and fusogenic trimer-of-hairpins structure will lessen the probability of changes conferring drug-resistance.

Influenza Pandemics

Influenza pandemics are caused by "antigenic shift", i.e., the introduction of new HA (or new HA and NA) subtypes into the human population. (Cox et al., Annu. Rev. Med., 51: 407-421 (2000)). The lack of prior exposure to the new HA (or HA and NA) subtypes creates a population that is immunologically naive to the "antigenic shift" variants, resulting in extremely high infection rates and rapid spread worldwide. In the 20th century, a total of three major pandemics have occurred: The 1918/1919 'Spanish influenza' is the most devastating infectious disease on record. An estimated 20-50 million people died worldwide and life expectancy in the US was reduced by 10 years. (Johnson et al., Bull. Hist. Med., 76: 105-115 (2000)). The causative agent of 'Spanish influenza' was H1N1 influenza A virus, which may have been introduced into human populations from an avian species. (Gamblin et al., Science, 303: 1838-1842 (2004); Reid et al., Nature Rev. Microbiol, 2: 909-914 (2004); Stevens et al., Science, 303: 1866-1870 (2004)). In 1957 and 1968, the 'Asian influenza' and 'Hong Kong influenza' killed an estimated 70,000 and 33,800 people in the US, respectively. (Johnson et al., 2002, supra). These two pandemic influenza virus strains also arose from reassortment of human and avian strains. (Scholtissek et al., Virology, 87: 13-20 (1978); Kawaoka et al., J. Virol., 63: 4603-4608 (1989); Nakajima et al., Nature, 274: 334-339 (1978)).

Outbreaks of Highly Pathogenic H5N1 Avian Influenza Viruses

Although highly pathogenic H5N1 viruses have not yet caused a human pandemic, their continued transmission to humans and high mortality rate in humans have made the development of therapies to these viruses a priority. The first transmission of highly pathogenic H5N1 avian influenza viruses to humans occurred in Hong Kong in 1997 when 6 of the 18 individuals infected succumbed to the infection. Since 2003, highly pathogenic H5N1 avian influenza viruses have become prevalent in Southeast Asia and endemic in poultry in some countries in this region. (Fauci, A. S., Cell, 124: 665-670 (2006)). More than 4200 outbreaks have been reported in Asian, African, and European countries resulting in the death or slaughter of >100 million poultry. (Beigel et al., 2005, supra). Close contact between humans and poultry in rural areas of these regions likely facilitate virus transmission to humans. 236 human infections with 138 fatalities have been reported in 9 different countries. (Beigel et al., 2005, supra). Furthermore, the appearance of oseltamivir (NA inhibitor) resistant strains of H5N1 indicates that novel therapeutic treatments are urgently needed. (Le et al., 2005, supra).

Options for Pandemic Control

An ideal way to combat the H5N1 avian influenza virus or any emerging or re-emerging influenza virus in humans is to inhibit or at least reduce the likelihood of interspecies transfer, and this requires a comprehensive, multifaceted approach. Currently, vaccination is the proven effective strategy for protection against influenza infection. However, its efficacy during a pandemic will be limited as a 'pandemic vaccine' cannot be developed in advance against new emerging strain(s). (Hayden, F. G., 2004, supra). The current inactivated trivalent vaccine does not provide protection against the H5 and H7 avian influenza strains. (Cox et al., 2005); Kemble, G., and H. Greenberg, 2003). Moreover, at this point we cannot predict whether the currently circulating H5N1 will be the next pandemic strain. In addition, the vaccine production capabilities will be strained during a pandemic by the need to immunize a vast number of individuals worldwide in a short period of time. Therefore, antiviral drugs are the first line of medical intervention.

Current anti-influenza drugs, oseltamivir and zanamivir efficiently block the NA activity of the 2004 H5N1 viruses in vitro indicating their effectiveness in influenza chemotherapy and prophylaxis against H5N1 virus infection. (Ward et al., 2005, supra; Mase et al., Virology, 332: 167-176 (2005); Gubareva et al., Lancet, 355: 827-835 (2000)). However, recent isolation of resistant mutants against these compounds has emphasized the urgent need for development of new antivirals. (Le et al., 2005, supra). Development of a new antiviral that will block the conserved receptor binding site or fusion domain of HA is a promising approach and will complement other mechanistic approaches.

Ebola Virus

Ebola viruses cause acute, lethal hemorrhagic fevers for which no vaccines or treatments currently exist. Ebola virus GP is a type I transmembrane glycoprotein. Comparisons of the predicted amino acid sequences for the GPs of the different Ebola virus strains show conservation of amino acids in the amino-terminal and carboxy-terminal regions with a highly variable region in the middle of the protein. (Feldmann et al., Virus Res., 24: 1-19 (1992)). The GP of Ebola viruses are highly glycosylated and contain both N-linked and O-linked carbohydrates that contribute up to 50% of the molecular weight of the protein. Most of the glycosylation sites are found in the central variable region of GP.

The membrane-anchored glycoprotein is the only viral protein known to be on the surfaces of virions and infected cells, and is presumed to be responsible for receptor binding and fusion of the virus with host cells. As a result, Ebola glycoprotein may be an important target preventing viral entry into a host cell. Development of a preventative treatment for Ebola virus is confounded by the observation that Ebola glycoprotein occurs in several forms. The transmembrane glycoprotein of Ebola viruses is unusual in that it is encoded in two open reading frames. Expression of glycoprotein occurs when the 2 reading frames are connected by transcriptional or translational editing. (Sanchez et al., Proc. Natl. Acad. Sci. USA 93: 3602-3607 (1996); Volchkov et al., Virology, 214: 421-430, (1995)). The unedited GP mRNA produces a non-structural secreted glycoprotein (sGP) that is synthesized in large amounts early during the course of infection. (Volchkov et al., 1995, supra; Sanchez et al., 1996, supra; Sanchez et al., J. Infect. Dis. 179 (suppl. 1, S164, (1999). Following editing, the virion-associated transmembrane glycoprotein is proteolytically processed into 2 disulfide-linked products. (Sanchez et al., J. Virol., 72: 6442-6447 (1998)). The amino-terminal product is referred to as $GP_1$ (140 kDa) and the carboxy-terminal cleavage product is referred to as $GP_2$ (26 kDa). $GP_1$ and membrane-bound GP, covalently associate to form a monomer of the GP spike found on the surfaces of virions. (Volchkov et al., Proc. Natl. Acad. Sci. USA 95: 5762 (1998); Sanchez et al., J. Virol., 72: 6442 (1998)). $GP_1$ is also released from infected cells in a soluble form. (Volchkov. et al., Virology, 245: 110 (1998)). sGP and $GP_1$ are identical in their first 295 N-terminal amino acids, whereas the remaining 69 C-terminal amino acids of sGP and 206 amino acids of $GP_1$ are encoded by different reading frames. Development of a new antiviral that will prevent receptor binding and fusion of the virus with a host cell is a promising approach for a vaccine against ebola and any virus with a similar mechanism for entering, i.e., infecting a host cell.

Vesicular Stomatitis Virus (VSV)

Vesicular Stomatitis Virus (VSV) is a non-segmented negative-stranded RNA virus and belongs to the family Rhabdoviridae, genus Vesiculovirus. VSV causes a contagious disease in horses, cattle, pigs, sheep and goats, characterized by vesicular lesions on the tongue, oral mucosa and udder and is transmitted by arthropod vectors. The prominent clinical presentation of vesicular stomatitis is the development of vesicles and ulcers in the oral cavity and, less frequently, on the teats and coronary bands. Mortality rates are typically very low, but production suffers because affected animals lose weight and may develop lameness or mastitis. The most significant concern with vesicular stomatitis is that, in cattle and pigs, it is clinically indistinguishable from foot and mouth disease and swine vesicular disease. Consequently, outbreaks of vesicular stomatitis lead to rapid imposition of international quarantines and shutoff of trade of animals and animals products.

There is also a public health concern because humans can be infected, Patterson, W. C., et al., J. Am. Vet. Med. Ass., 133, 57 (1958), and the virus may be spread by insect vectors, Ferris et al., J. Infect. Dis., 96, 184 (1955), Tesh et al., Science, 175, 1477 (1972).

VSV contains a single negative strand of ribonucleic acids (RNA), which encodes 5 messenger RNA's (mRNA's) and its eleven kb genome has five genes which encode five structural proteins of the virus: the nucleocapsid protein (N), which is required in stoichiometric amounts for encapsidation of the replicated RNA; the phosphoprotein (P), which is a cofactor of the RNA-dependent RNA polymerase (L); the matrix protein (M) and the attachment glycoprotein (G) (e.g., see Gallione et al., 1981 J. Virol., 39:529-535; Rose and Gallione, 1981, J. Virol., 39:519-528; U.S. Pat. No. 6,033, 886; U.S. Pat. No. 6,168,943).

The vesicular stomatitis virus envelope protein G binds to the host cell surface to initiate infection. The viral envelope protein participates in virus binding to and/or entry of the infectious virus into a host cell.

Interfering with virus entry is a novel and attractive therapeutic strategy to control virus infection. Proof of principle of this approach has come from peptidic HIV inhibitor enfuvirtide. While confirming the therapeutic benefit of entry inhibitors for the treatment of viral infections, enfuvirtide has also highlighted potential problems of peptidic antivirals. Large heptad repeat-derived peptides, like enfuvirtide, are costly to manufacture, and poor absorption from the gastrointestinal tract necessitates i.v. delivery.

SUMMARY OF THE INVENTION

The present invention relates to the development of non-peptidic small molecules to inhibit virus entry into a host cell. Multiple routes of administration are conceivable for these drug-like molecules, and highly cost-effective production strategies can be easily achieved. Conceptual support for this approach comes from the previous identification of several small molecules that interfere with paramyxovirus entry. (Plemper et al., Antimicrob. Agents Chemother., 49: 3755-3761 (2005); Plemper et al., Proc. Natl. Acad. Sci. USA, 101: 5628-5633 (2004); Cianci et al., Proc. Natl. Acad. Sci. USA, 101: 15046-15051 (2004); Cianci et al., Antimicrob. Agents Chemother., 48: 413-422 (2004)). HA is a class I fusion protein as are HIV Gp120 and F protein of paramyxoviruses. (Cianci et al., 2004, supra). Class I fusion proteins undergo a series of conformational rearrangements that leads to the association of C- and N-terminal heptad repeats. The resultant structure, a stable six-helix bundle, promotes the juxtaposition of the viral and cellular envelopes during fusion. This final fusion hairpin structure is sustained by protein-protein interactions. Small molecule entry inhibitors of paramyxoviruses have been identified that interfere with the formation or consolidation of the final fusion hairpin structure. (Plemper et al., 2005, supra; Cianci et al., 2004, supra). Because a similar structure is present in different class I fusion proteins, including influenza HA, these results support the hypothesis of targeting HA as a strategy for drug discovery.

Antiviral drugs will be the first line of medical intervention in the event of a pandemic. Combinatorial use of multiple drugs that have different mechanisms of antiviral activity will be required for synergistic antiviral effects to prevent the emergence of resistant strains. Therefore, there is urgent need for new drugs to counter a new pandemic. In addition, the worldwide market for antiviral drugs is estimated to be approximately $10 billion/year (Datamonitor) and expected to grow rapidly as new therapies become available.

Therefore, broad-spectrum therapeutics against virus infections are critically needed to address the problem of pandemics, a major threat to the public health globally. The discovery and development of inhibitors of viral infection, as outlined herein, will provide life-saving therapy worldwide and prove invaluable in dealing with a potentially catastrophic pandemic. Interfering with virus entry as described herein is a novel and attractive therapeutic strategy to control virus infection and due to the similar mechanisms of host cellular entry for RNA envelope viruses, it is believed that similar small molecule inhibitors would be effective for preventing entry of a number of these types of viruses into a host cell. Examples of viruses that the small molecule inhibitors of the present invention would be effective at preventing infection of a host cell include, but are not limited to, influenza virus, e.g., avian H5N1 influenza virus, ebola virus, vesicular stomatitis virus (VSV), and SARS.

Therefore, the present invention is related to the discovery of novel nonpeptidic small molecule inhibitor compounds and methods for treating or preventing viral infection comprising administering the compounds to an individual, i.e., mammal, in need thereof. In another embodiment, the present invention is directed to the discovery of noel nonpeptidic small molecule inhibitor compounds and methods for treating or preventing, i.e., inhibiting, viral entry into a host cell comprising administration the inhibitor compounds described herein to an individual, i.e., mammal, in need thereof.

In another embodiment, the present invention is related to the discovery of novel nonpeptidic small molecule inhibitors that prevent entry of influenza virus into a mammalian host cell. In a particularly preferred embodiment, the novel nonpeptidic small molecules inhibit entry, i.e., infection, of the avian H5N1 influenza virus subtype in a human. The inhibitors described herein are suitable for the treatment and/or prevention of the avian H5N1 influenza virus in mammals, and in particular, humans.

In another preferred embodiment, the present invention is related to the discovery of novel nonpeptidic small molecule inhibitors that prevent entry of ebola virus into a mammalian host cell, preferably a human host cell. The inhibitors described herein are suitable for the treatment and/or prevention of ebola virus infection in mammals, and in particular, humans.

In another preferred embodiment, the present invention is related to the discovery of novel nonpeptidic small molecule inhibitors that prevent entry of vesicular stomatitis virus (VSV) into a mammalian host cell, preferably a human host cell. The inhibitors described herein are suitable for the treatment and/or prevention of the vesicular stomatitis virus infection in mammals, and in particular, humans.

The nonpeptidic small molecule inhibitors of viral entry into host cells according to the present invention are compounds comprising Formula I:

Formula I wherein:

$Ar^1$ and $Ar^2$ are independently a monovalent aryl or heteroaryl moiety which may be unsubstituted or substituted by up to 5 substituents selected from halo, amino, amidino, guanidino, alkyl, haloalkyl, alkenyl, alkynyl, cycloalkyl, heterocycloalkyl, aryl, heteroaryl, hydroxy, alkoxy, aryloxy, heteroaryloxy, acyl, carboxy, alkoxycarbonyl, aryloxycarbonyl, amino, alkylamino, acylamino, amido, sulfonamido, mercapto, alkylthio, arylthio, hydroxamate, thioacyl, alkylsulfonyl, and aminosulfonyl, and $R^1$ is a monovalent alkyl, haloalkyl, alkenyl, alkynyl, cycloalkyl, heterocycloalkyl, aryl, or heteroaryl moiety that may be unsubstituted or additionally substituted by one or more of the following substituents selected from: cycloalkyl, heterocycloalkyl, aryl, heteroaryl, hydroxy, alkoxy, aryloxy, heteroaryloxy, acyl, carboxy, alkoxycarbonyl, aryloxycarbonyl, amino, alkylamino, acylamino, amido, sulfonamido, mercapto, alkylthio, arylthio, hydroxamate, thioacyl, alkylsulfonyl, and aminosulfonyl, and $R^2$ and $R^3$ are independently selected from hydrogen or an alkyl, haloalkyl, alkenyl, alkynyl, cycloalkyl, heterocycloalkyl, hydroxy, alkoxy, amino, alkylamino, and acylamino moiety, and $R^4$ is selected from hydrogen or a monovalent alkyl, haloalkyl, alkenyl, alkynyl, cycloalkyl, and heterocycloalkyl moiety;

and wherein:

substituents $R^2$ and $R^3$ may be joined to form carbocyclic or heterocyclic rings and if substituents $R^2$ and $R^3$ are different, the enantiomer may be of either the (R)- or (S)-configuration, or a racemic compound;

and pharmaceutically acceptable salts thereof.

In another embodiment, the present invention is related to a method for treating or preventing viral entry into a host cell, i.e., viral infection, comprising administration of the nonpeptidic small molecule inhibitors of Formula I. In a preferred embodiment, the present invention is related to a method for treating or preventing entry of influenza virus in a mammalian host cell by administration of the nonpeptidic small molecule inhibitor compounds of Formula I. In a particularly preferred embodiment, the present invention is directed to a method for treating or preventing the entry, i.e., infection of the avian influenza virus H5N1 subtype in a human by administration of the nonpeptidic small molecule inhibitors of Formula I. The method described herein is suitable for the treatment and/or prevention of the avian H5N1 influenza virus in mammals, and in particular, humans.

In another embodiment, the present invention is related to a method for treating or preventing entry of ebola virus, i.e., infection, in a mammalian host cell by administration of the nonpeptidic small molecule inhibitor compounds of Formula I. In a particularly preferred embodiment, the present invention is directed to a method for preventing the entry, i.e., infection of the ebola virus in a human by administration of the nonpeptidic small molecule inhibitor compounds of Formula I. The method described herein is suitable for the treatment and/or prevention of ebola virus infection in mammals, and in particular, humans.

In yet another embodiment, the present invention is related to a method for treating or preventing entry of vesicular stomatitis virus, i.e., infection, in a mammalian host cell by administration of the nonpeptidic small molecule inhibitor compounds of Formula I. In a particularly preferred embodiment, the present invention is directed to a method for preventing the entry, i.e., infection of the vesicular stomatitis virus in a human by administration of the nonpeptidic small molecule inhibitor compounds of Formula I. The method described herein is suitable for the treatment and/or prevention of vesicular stomatitis virus infection in mammals, and in particular, humans.

In a preferred embodiment, where it is desirable to prevent the entry of the avian H5N1 influenza virus into a human, the inhibitors of the present invention will target, i.e., be specific for, the hemagglutinin (HA) envelope glycoprotein that mediates viral entry into the cell. However, it will be appreciated that, by following the procedures described herein, nonpeptidic small molecule inhibitors for any influenza virus, virus subtype, or viral target can be identified.

To identify inhibitors that prevent entry of the H5N1 virus into host cells, a pseudotype virus expressing HA (H5 subtype) was developed as a model to mimic HA-mediated entry of the live virus into a cell. The pseudotype virus provides a means for safely replicating the viral entry mechanism and identifying inhibitors thereof, which inhibitors can then be tested against live viral infection under strict regulatory conditions that are not required for initial screenings with the pseudotype viruses.

Therefore, by following the procedures described herein, a HTS assay has been developed using HIV/HA(H5) to screen for HA (H5) inhibitors. 36 HA(H5) specific inhibitors have been identified with $IC_{90}<25$ µM and $CC_{50}>25$ µM and all 36 compounds inhibited cell culture grown influenza virus (H1N1)(PR8).

In addition, a number of inhibitors have been identified that prevent viral entry of ebola virus and vesicular stomatitis virus into a host cell. (See, FIG. 4.)

A preferred viral entry inhibitor compound of this invention has the structure shown in FIG. 12.

In another embodiment, the inhibitor compounds of the present invention are formulated into a pharmaceutically-acceptable carrier or excipient and are applied by injection, including, without limitation, intradermal, transdermal, intramuscular, intraperitoneal and intravenous. According to another embodiment of the invention, the administration of the inhibitor compounds may be by oral administration and the vaccine may be presented, for example, in the form of a tablet or encased in a gelatin capsule or a microcapsule, which simplifies oral application. The production of these forms of administration is within the general knowledge of a technical expert. Multiple routes of administration are envisioned for these drug-like molecules, and highly cost-effective production strategies can be easily achieved.

The data presented herein showing that the claimed sulfonamide compounds inhibit influenza, ebola, and vesicular stomatitis virus infection, indicate that the class of sulfonamide compounds of Formula I will be effective to inhibit infectivity, i.e., host cell entry, of a range of viruses, including but not limited to RNA enveloped viruses. RNA enveloped viruses are similar in that all have type1 membrane protein and utilize a similar mechanism for host cell entry, namely by receptor mediated endocytosis followed by acid lysis for release into the cytoplasm. While not being limited to any particular theory, it is believed that the sulfonamide compounds described herein effectively block this mechanism of viral infectivity.

Therefore the data presented herein demonstrating that the compounds of Formula I prevent viral entry of avain H5N1 influenza virus, ebola virus, and vesicular stomatitis virus into a host cell are merely representative of the types of viruses that can be inhibited according to the present invention and, as such, one skilled in the art would recognize that the inhibitor compounds described herein would be suitable for preventing viral entry into a host cell of a number of other types of viruses, in particular viruses that utilize the entry mechanism described above for RNA enveloped viruses, for example, SARS virus.

BRIEF DESCRIPTION OF THE DRAWINGS

FIG. 9 shows the development of an HA binding assay to susceptible cells to elucidate the mode of HA/inhibitor interactions.

FIG. 11 is workflow diagram for advancing small compound "hits" from the initial screening stage with HIV/HA to an HA specific influenza inhibitor.

DEFINITIONS

Figure 1:
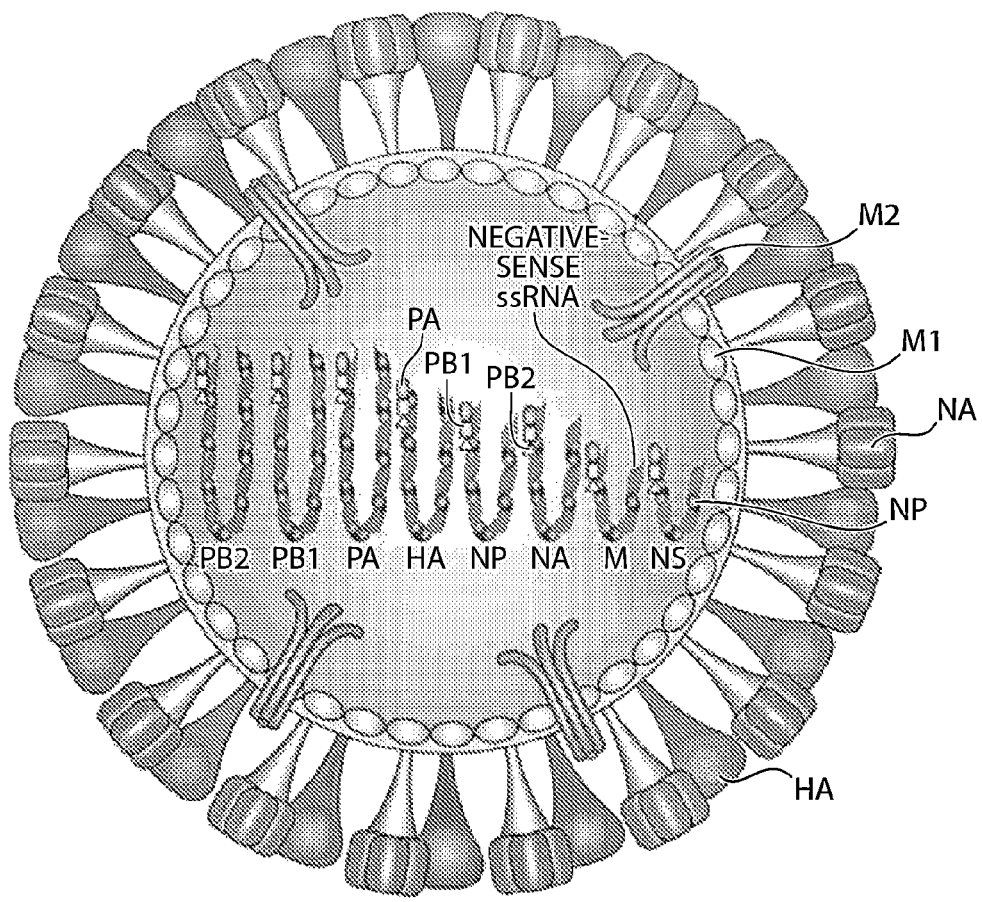
FIG. 1 is a schematic diagram of the influenza A virus.
Figure 2:
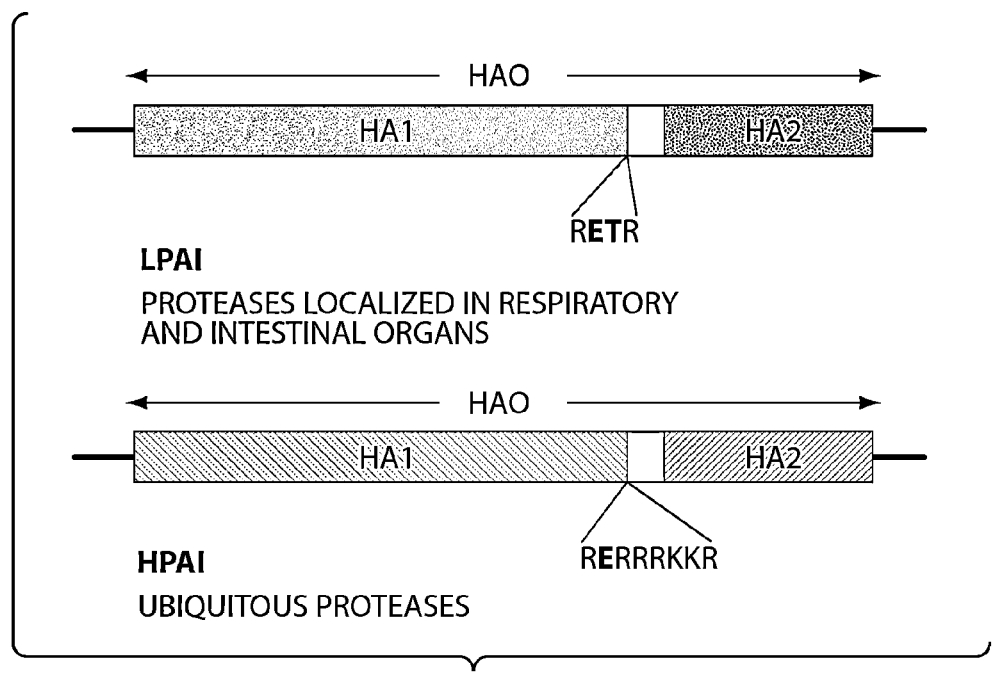
FIG. 2 is a schematic illustration of the post-translational proteolytic cleavage sites of the HA precursor molecules in highly pathogenic avian influenza (HPAI) viruses and low-pathogenic avian influenza (LPAI) viruses.

The term "halo" or "halogen" indicates fluorine, chlorine, bromine, or iodine.

"Alkyl" refers to a straight or branched chain monovalent or divalent radical of saturated and/or unsaturated carbon atoms and hydrogen atoms, such as methyl (Me), ethyl (Et), propyl (Pr), isopropyl (iPr), butyl (Bu), isobutyl (iBu), secbutyl (sBu), tert-butyl (tBu), and the like, which may be unsubstituted, or substituted by one or more suitable substituents found herein.

"Haloalkyl" refers to an alkyl moiety that is substituted with one or more identical or different halogen atoms, e.g., —CH$_2$Cl, —CF$_3$, —CH$_2$CF$_3$, —CH$_2$CCl$_3$, and the like.

"Alkenyl" refers to a straight-chain, branched, or cyclic hydrocarbon radical having from between 2-8 carbon atoms and at least one double bond, e.g., ethenyl, 3-buten-1-yl, 3-hexen-1-yl, cyclopent-1-en-3-yl, and the like, which may be unsubstituted, or substituted by one or more suitable substituents found herein.

"Alkynyl" refers to a straight-chain or branched hydrocarbon radical having from between 2-8 carbon atoms an at least one triple bond, e.g., ethynyl, 3-butyn-1-yl, 2-butyn-1-yl, 3-pentyn-1-yl, and the like, which may be unsubstituted, or substituted by one or more suitable substituents found herein.

"Cycloalkyl" refers to a non-aromatic monovalent or divalent monocyclic or polycyclic radical having from between 3-12 carbon atoms, each of which may be saturated or unsaturated, e.g., cyclopentyl, cyclohexyl, decalinyl, and the like, unsubstituted, or substituted by one or more of the suitable substituents found herein, and to which may be fused one or more aryl groups, heteroaryl groups, or heterocycloalkyl groups, which themselves may be unsubstituted or substituted by one or more suitable substituents found herein.

"Heterocycloalkyl" refers to a non-aromatic monovalent or divalent, monocyclic or polycyclic radical having from between 2-12 carbon atoms, and between 1-5 heteroatoms selected from nitrogen, oxygen, or sulfur, each of which may be saturated or unsaturated, e.g., pyrrolodinyl, tetrahydropyranyl, morpholinyl, piperazinyl, oxiranyl, and the like, unsubstituted, or substituted by one or more of the suitable substituents found herein, and to which may be fused one or more aryl groups, heteroaryl groups, or heterocycloalkyl groups, which themselves may be unsubstituted or substituted by one or more suitable substituents found herein.

"Aryl" refers to an aromatic monovalent or divalent monocyclic or polycyclic radical comprising between 6 and 18 carbon ring members, e.g., phenyl, biphenyl, naphthyl, phenanthryl, and the like, which may be substituted by one or more of the suitable substituents found herein, and to which may be fused one or more heteroaryl groups or heterocycloalkyl groups, which themselves may be unsubstituted or substituted by one or more suitable substituents found herein.

"Heteroaryl" refers to an aromatic monovalent or divalent monocyclic or polycyclic radical comprising between 2 and 18 carbon ring members and at least 1 heteroatom selected from nitrogen, oxygen, or sulfur, e.g., pyridyl, pyrazinyl, pyridizinyl, pyrimidinyl, furanyl, thienyl, triazolyl, quinolinyl, imidazolinyl, benzimidazolinyl, indolyl, and the like, which may be substituted by one or more of the suitable substituents found herein, and to which may be fused one or more aryl, heteroaryl groups or heterocycloalkyl groups, which themselves may be unsubstituted or substituted by one or more suitable substituents found herein.

"Hydroxy" indicates the radical —OH.

"Alkoxy" indicates the radical —OR where R is an alkyl or cycloalkyl group.

"Aryloxy" indicates the radical —OAr where Ar is an aryl group.

"Heteroaryloxy" indicates the radical —O(HAr) where HAr is a heteroaryl group.

"Acyl" indicates a —C(O)R radical where R is alkyl, alkenyl, alkynyl, cycloalkyl, aryl, heteroaryl, or heterocycloalkyl, e.g. acetyl, benzoyl, and the like.

"Carboxy" refers to the radical —C(O)OH.

"Alkoxycarbonyl" refers to a —C(O)OR radical where R is alkyl, alkenyl, alkynyl, or cycloalkyl.

"Aryloxycarbonyl" refers to a —C(O)OR radical where R is aryl or heteroaryl.

"Amino" refers to the radical —NH$_2$.

"Alkylamino" refers to the radical —NRR' where R, and R' are, independently, hydrogen, alkyl, alkenyl, alkynyl, cycloalkyl, aryl, or heteroaryl, or heterocycloalkyl.

"Acylamino" refers to the radical —NHC(O)R, where R is alkyl, alkenyl, alkynyl, cycloalkyl, aryl, heteroaryl, or heterocycloalkyl, e.g. acetyl, benzoyl, and the like, e.g., acetylamino, benzoylamino, and the like.

"Amido" refers to the radical —C(O)NRR' where R and R' are, independently, hydrogen, alkyl, alkenyl, alkynyl, cycloalkyl, aryl, or heteroaryl, or heterocycloalkyl.

"Sulfonylamino" refers to the radical —NHSO$_2$R where R is alkyl, alkenyl, alkynyl, cycloalkyl, aryl, heteroaryl, or heterocycloalkyl.

"Amidino" refers to the radical —C(NR)NR'R", where R, R', and R" are, independently, hydrogen, alkyl, alkenyl, alkynyl, cycloalkyl, aryl, or heteroaryl, and wherein R, R', and R" may form heterocycloalkyl rings, e.g. carboxamido, imidazolinyl, tetrahydropyrimidinyl.

"Guanidino" refers to the radical —NHC(NR)NR'R", where R, R', and R" are, independently, hydrogen, alkyl, alkenyl, alkynyl, cycloalkyl, aryl, or heteroaryl, and wherein R, R', and R" may form heterocycloalkyl rings.

"Mercapto" refers to the radical —SH.

"Alkylthio" refers to the radical —SR where R is an alkyl or cycloalkyl group.

"Arylthio" indicates the radical —SAr where Ar is an aryl group.

"Hydroxamate" refers to the radical —C(O)NHOR where R is an alkyl or cycloalkyl group.

"Thioacyl" refers to a —C(S)R radical where R is alkyl, alkenyl, alkynyl, cycloalkyl, aryl, heteroaryl, or heterocycloalkyl.

"Alkylsulfonyl" refers to the radical —SO$_2$R where R is alkyl, alkenyl, alkynyl, cycloalkyl, aryl, heteroaryl, or heterocycloalkyl.

"Aminosulfonyl" refers to the radical —SO$_2$NRR' where R and R' are, independently, hydrogen, alkyl, alkenyl, alkynyl, cycloalkyl, aryl, or heteroaryl, or heterocycloalkyl.

DETAILED DESCRIPTION OF THE INVENTION

The present invention is related to the discovery of novel nonpeptidic small molecule inhibitors of viral infection. More particularly, the present invention is related to the discovery of novel nonpeptidic small molecule inhibitors and methods for preventing viral entry, i.e., infection, into host cells.

In one embodiment, the present invention is related to the discovery of novel nonpeptidic small molecule inhibitors that prevent entry of influenza virus into a mammalian host cell. In a particularly preferred embodiment, the nonpeptidic small molecules inhibit entry, i.e., infection of the avian H5N1 influenza virus subtype in a human. The inhibitors described herein are suitable for in a method for the treatment and/or prevention of the avian H5N1 influenza virus in mammals, and in particular, humans, by administration of the small molecule inhibitors described herein.

In another embodiment, the present invention is related to the discovery of novel nonpeptidic small molecule inhibitors that prevent entry of ebola virus into a mammalian host cell, preferably a human host cell. The inhibitors described herein are suitable in a method for the treatment and/or prevention of the ebola virus in mammals, and in particular, humans by administration of the inhibitors disclosed herein.

In another embodiment, the present invention is related to the discovery of novel nonpeptidic small molecule inhibitors that prevent entry of vesicular stomatitis virus into a mammalian host cell, preferably a human host cell. The inhibitors described herein are suitable in a method for the treatment and/or prevention of the vesicular stomatitis virus in mammals, and in particular, humans by administration of the inhibitors disclosed herein.

The potential pandemic of bird flu H5N1 is a global public health concern. No licensed human vaccines are yet available for H5N1 viruses, and studies conducted with inactivated H5N1 vaccines to date suggest these test vaccines have low immunogenicity. Therefore, emergence of drug-resistant H5N1 strains in human patients is a wake-up call for developing new anti-H5N1 (and other flu) therapeutics. (Le et al., 2005, supra). The strategy described herein for developing new anti-influenza therapeutics is to target the surface protein hemagglutinin (HA), which mediates influenza virus entry through receptor binding and fusion of the virus with host cells. (Lamb, R. A., 2001, supra; Wright, P. F., 2001, supra).

The present invention describes the isolation and identification of nonpeptidic small molecules that function to inhibit virus entry into a host cell. Conceptual support for this approach comes from the previous identification of several small molecules that interfere with RSV and MV entry. (Plemper et al., 2005, supra; Plemper et al., 2004, supra; Clanci et al., 2004, supra; Clanci et al., Antimicrob. Agents Chemother., 48: 413-422 (2004)). HA is a class I fusion protein, a class that includes HIV Gp120 and F protein of paramyxoviruses (RSV and MV). (Lamb, R. A., 2001, supra; Wright, P. F., 2001, supra; Cianci et al., 2004, supra).

Class I fusion proteins undergo a series of conformational rearrangements resulting in a stable six-helix bundle fusion structure that is maintained through protein-protein interactions. (Clanci et al., 2004, supra). Small molecule entry inhibitors of RSV and MV have been identified that interfere with the formation or consolidation of the final fusion hairpin structure. (Plemper et al., Proc. Natl. Acad. Sci. USA, 101: 5628-33 (2004); Clanci et al., 2004, supra). Because analogous structures are present in other class I fusion proteins, including influenza HA, discovery of these inhibitors support the hypothesis of targeting HA as a strategy for drug discovery.

The invention provides specific organic compounds that inhibit viral entry into a host cell. By following the procedures outlined herein, a series of compounds having a sulfonamide scaffold were discovered that prevent viral entry, i.e., infection of a host cell.

The compounds of the present invention comprise the structure of Formula I:

Formula I wherein:

$Ar^1$ and $Ar^2$ are independently a monovalent aryl or heteroaryl moiety which may be unsubstituted or substituted by up to 5 substituents selected from halo, amino, amidino, guanidino, alkyl, haloalkyl, alkenyl, alkynyl, cycloalkyl, heterocycloalkyl, aryl, heteroaryl, hydroxy, alkoxy, aryloxy, heteroaryloxy, acyl, carboxy, alkoxycarbonyl, aryloxycarbonyl, amino, alkylamino, acylamino, amido, sulfonamido, mercapto, alkylthio, arylthio, hydroxamate, thioacyl, alkylsulfonyl, and aminosulfonyl, and $R^1$ is a monovalent alkyl, haloalkyl, alkenyl, alkynyl, cycloalkyl, heterocycloalkyl, aryl, or heteroaryl moiety that may be unsubstituted or additionally substituted by one or more of the following substituents selected from: cycloalkyl, heterocycloalkyl, aryl, heteroaryl, hydroxy, alkoxy, aryloxy, heteroaryloxy, acyl, carboxy, alkoxycarbonyl, aryloxycarbonyl, amino, alkylamino, acylamino, amido, sulfonamido, mercapto, alkylthio, arylthio, hydroxamate, thioacyl, alkylsulfonyl, and aminosulfonyl, and $R^2$ and $R^3$ are independently selected from hydrogen or an alkyl, haloalkyl, alkenyl, alkynyl, cycloalkyl, heterocycloalkyl, hydroxy, alkoxy, amino, alkylamino, and acylamino moiety, and $R^4$ is selected from hydrogen or a monovalent alkyl, haloalkyl, alkenyl, alkynyl, cycloalkyl, and heterocycloalkyl moiety;

and wherein:

substituents $R^2$ and $R^3$ may be joined to form carbocyclic or heterocyclic rings and if substituents $R^2$ and $R^3$ are different, the enantiomer may be of either the (R)- or (S)-configuration, or a racemic compound;

and pharmaceutically acceptable salts thereof.

It is preferable to develop an orally active therapeutic (tablet or liquid), since that is the most convenient and rapid method to administer a drug to a large exposed population in case of pandemic. However, the inhibitors described herein will also be suitable for IV administration, because it is envisioned that in the case of a natural outbreak, the infected patients may require IV administration. Therefore, the inhibitors described herein will provide an effective, safe, and easy therapeutic option for any newly emerged pandemic strain(s).

For oral administration, the pharmaceutical compositions may take the form of, for example, tablets or capsules prepared by conventional means with pharmaceutically acceptable carriers or excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol) and preservatives (e.g., methyl or propyl p-hydroxybenzoates or sorbic acid).

A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or which "consists of") the named elements or steps to the exclusion of any other unnamed element or step. In any composition or method disclosed herein, known or disclosed equivalents of any named essential element or step may be substituted for that element or step. It is also understood that an element or step "selected from the group consisting of" refers to one or more of the elements or steps in the list that follows, including combinations of any two or more of the listed elements or steps.

The meaning of other terms will be understood by the context as understood by the skilled practitioner in the art, including the fields of organic chemistry, pharmacology, and microbiology.

The present invention is related to the discovery of nonpeptidic small molecule inhibitors, that prevent viral entry into a host cell. The class of sulfonamide compounds of Formula I will be effective to inhibit infectivity, i.e., host cell entry, of a range of viruses, including but not limited to RNA enveloped viruses. RNA enveloped viruses are similar in that all have type1 membrane protein and utilize a similar mechanism for host cell entry, namely by receptor mediated endocytosis followed by acid lysis for release into the cytoplasm. Influenza virus, ebola virus, and vascular stomatitis virus are representative examples of RNA enveloped viruses that utilize this mechanism entry. While not being limited to any particular theory, it is believed that the sulfonamide compounds described herein effectively block this mechanism of viral infectivity. Therefore, it will be appreciated by one skilled in the art that the sulfonamide compounds of Formula I described herein will be effective at inhibiting infectivity of host cells by this class of viruses, namely the RNA enveloped viruses, which include, for example, SARS virus.

In another embodiment, the present invention is related to the discovery of nonpeptidic small molecule inhibitors and methods for treating or preventing infection of influenza virus. The inhibitors described herein are suitable for the treatment and/or prevention of influenza virus. More particularly, the inhibitors described herein are suitable for the treatment and/or prevention of influenza virus in humans. Specifically the invention is related to the identification and characterization of nonpeptidic small molecules (inhibitors) that prevent entry of the virus into a host cell. Even more particularly, the invention is related to the identification of nonpeptidic small molecule inhibitors for preventing the entry of avian influenza H5N1 subtype into a host cell. In a preferred embodiment, the inhibitors of the present invention will target, i.e., be specific for, the hemagglutinin (HA) envelope glycoprotein that mediates viral entry into the cell. However, it will be appreciated that, by following the procedures described herein, nonpeptidic small molecule inhibitors can be identified for not only any influenza virus or influenza virus subtype, but other viruses such as, for example, but not limited to, ebola virus and vesicular stomatitis virus.

In another embodiment, the present invention is related to the discovery of nonpeptidic small molecule inhibitors and methods for treating or preventing infection of ebola virus. The inhibitors described herein are suitable for the treatment and/or prevention of ebola virus infection in mammals. More particularly, the inhibitors described herein are suitable for the treatment and/or prevention of ebola virus infection in humans. Specifically the invention is related to the identification and characterization of nonpeptidic small molecules (inhibitors) that prevent entry of the ebola virus into a host cell. However, it will be appreciated by one skilled in the art that by following the procedures described herein, nonpeptidic small molecule inhibitors for preventing host infection by any virus or virus subtype can be identified.

In another embodiment, the present invention is related to the discovery of nonpeptidic small molecule inhibitors and methods for treating or preventing infection of vesicular stomatitis virus (VSV). The inhibitors described herein are suitable for the treatment and/or prevention of VSV infection in mammals. More particularly, the inhibitors described herein are suitable for the treatment and/or prevention of VSV infection in humans. Specifically the invention is related to the identification and characterization of nonpeptidic small molecules (inhibitors) that prevent entry of VSV into a host cell. However, it will be appreciated by one skilled in the art that by following the procedures described herein, nonpeptidic small molecule inhibitors for preventing host infection by any virus or virus subtype can be identified.

The following describes the construction of a pseudotype virus to identify inhibitor compounds for preventing entry of avian influenza virus H5N1 into a host cell. However, it will be appreciated by one skilled in the art that the procedures described below are suitable to identify inhibitor compounds to prevent entry of any of a number of viruses including, but not limited to, ebola virus and vesicular stomatitis virus, into a host cell.

Identification of Inhibitors to Avian Influenza Virus H5N1.

To identify inhibitors that prevent entry of the H5N1 virus into host cells, a pseudotype virus expressing HA (H5 subtype) was developed as a model to mimic HA-mediated entry of the live virus into a cell. The pseudotype virus provides a means for safely replicating the viral entry mechanism and identifying inhibitors thereof, which inhibitors can then be tested against live viral infection under strict regulatory conditions that are not required for initial screenings with the pseudotype viruses.

To construct the pseudotype virus, cDNA encoding the HA gene of the highly pathogenic H5N1 influenza virus in migratory birds was cloned into the pcDNA3 mammalian expression vector under the control of the CMV promoter. To generate an HIV derived influenza pseudotype expressing HA (HIV/HA), the HIV-1 proviral genome containing a luciferase reporter gene (pNL4.3.Luc.R−E−) was co-transfected with the H5 HA (pcDNA3-HA) into 293T cells. The HIV/HA contains a luciferase gene reporter gene. Upon entry into a target cell, the viral RNA is reverse transcribed, actively imported into the nucleus, and stably integrated into the genome. Luciferase activity in the transduced cells provides a measure of virus infectivity. (Basu et al., J. Virol., 81: 3933-3941 (2007); Manicassamy et al., J. Virol., 79: 4793-4805 (2005)). The luciferase assay is highly sensitive and is suitable for a high throughput screening (HTS) 96-well plate format. In addition, the use of non-replicating HIV derived influenza pseudotypes make HTS feasible without the need for stringent biohazard conditions required for handling pathogenic avian influenza strains. This is a key advantage of HIV/HA for developing an HTS assay to measure virus attachment and entry.

The present application also addresses the optimization of several important parameters related to the discovery of small molecule inhibitors according to the present invention including: (a) generation of HIV/HA (b) target cells to be used (c) titration of HIV/HA and (d) controls to maximize infectivity and signal to background (S/B) ratio (>100/1).

Following construction of HIV/HA, the pseudotype virus was collected and assessed for infectivity following standard protocols. A particular advantage of the pseudotype virus is it provides a means to safely and reliably mimic the entry of the "live" virus into a host cell while eliminating the dangers of working directly with the live virus. Eventually potential inhibitors identified in this early screening process will be tested for the ability to prevent entry of the live virus into a host cell, however these later tests will be conducted under strict regulatory conditions which are not required for working with the pseudotype virus. Therefore, "primary hits" of inhibitors from the pseudotype virus assays will then be evaluated against infectious low pathogenic avian H5N2 isolate and against a recombinant H5N1 strain in an enhanced BSL3 laboratory. This secondary screening will rapidly identify only those compounds that are active against infectious viruses.

Another advantage of conducting the initial screening with the pseudotype virus as opposed to the live infectious virus is that working with the live virus will lead to the identification of compounds that will not only inhibit viral entry, but also viral replication and egress. The initial screen is performed with a compound library of >100,000 compounds for entry inhibition, thus even a small increase in the number of primary hits (due to presence of replication and assembly inhibitors) could result in the necessity for additional secondary testing of thousands of compounds. In contrast, initial screening with the pseudotype virus as described herein reduces the number of primary hits because it will identify only putative entry inhibitors of H5 influenza virus. Therefore, the method of primary screening with pseudotype virus reduced both the number of compounds handled and the screens needed.

In another aspect, the present invention is directed to a high throughput system (HTS) assay for rapidly screening potential small molecule inhibitors of influenza virus using the pseudotype viruses described herein. However, it will appreciated by one skilled in the art that the high throughput assay described herein may be adapted to identify inhibitor compounds that prevent viral entry into a host cell, for example, but not limited to, inhibitor compounds that prevent entry of the ebola virus or vesicular stomatitis virus into a host cell. Therefore, the assay described herein provides a valuable tool for identifying viral inhibitory compounds having the potential for treating or preventing a wide variety of viruses-related illnesses in mammals, especially humans.

It is an object of the present invention to target envelope glycoprotein hemagglutinin (HA), which mediates influenza virus entry through receptor binding and fusion with host cells. The focus of this application is to discover anti-H5N1 entry inhibitors and to develop entry therapeutics for H5N1 and other potential pandemic influenza viruses. HA displays significant variation (>30%) among subtypes, but the important domains for receptor attachment and fusion are conserved. (Fauci, A. S., 2006, supra; Lamb, R. A., 2001, supra; Wright, P. F., 2001, supra).

Therefore, targeting of these conserved regions will lessen the probability of resistance development.

In another embodiment, the present invention is directed to the identification of a broad spectrum anti-influenza inhibitor that may not have a well-defined mechanism of action. It is envisioned that this type of inhibitor will be suitable for further testing as a potential influenza virus inhibitor while the mechanism of action is further elucidated.

Following the procedures outlined below, approximately 40,000 discrete compounds were screened and 141 primary hits identified. The Z' factor for the HTS was 0.5±0.2. Primary hits were counter-screened with pseudotype virus expressing an unrelated glycoprotein (VSV-G) and infectious H1N1 virus for their specificity. They were evaluated for their potency, and cytotoxicity with resynthesized compounds. Only 36 of the primary hits specifically inhibited the HA mediated entry process. The final hit rate from the HTS was 0.09%. All the 36 hit compounds exhibited $IC_{90}$ values of ≤25 μM. Structurally, the HA inhibitors can be represented as clusters of ≥2 members each and singletons.

Therefore, by following the procedures described herein, a HTS assay has been developed using HIV/HA(H5) to screen for HA (H5) inhibitors. 36 HA(H5) specific inhibitors have been identified with $IC_{90}$<25 μM and $CC_{50}$>25 μM and all 36 compounds inhibited cell culture grown influenza virus (H1N1)(PR8).

Figure 12:
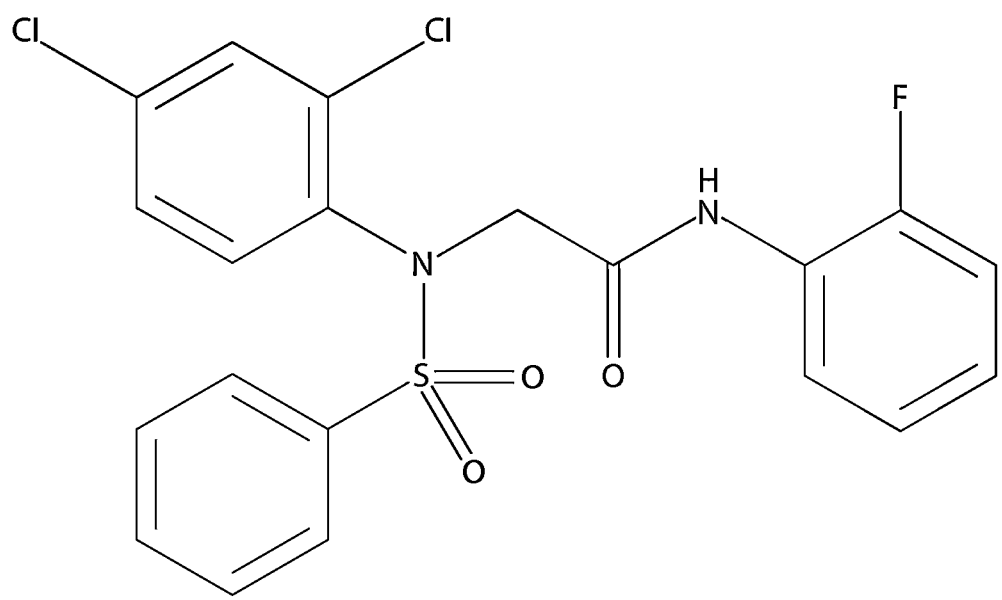
FIG. 12 shows the structure of isolated Compound 2, used as a preliminary SAR scaffold to study analogous small molecule inhibitor compounds identified according to the present invention as described in Example 9.

A preferred viral entry inhibitor compound of this invention has the structure shown in FIG. 12.

EXAMPLES

Example 1

Establishment of HIV/HA Pseudotyping System for H5N1 Avian Influenza Entry

Influenza Virus HA Used in this Study.

The cDNA encoding the HA (H5) gene of the highly pathogenic H5N1 influenza virus, was kindly provided by Dr. George Gao, Institute of Microbiology, Chinese Academy of Sciences, China. This HA gene was originally isolated from an influenza A H5N1 virus present in a dead migratory bird (goose) in Qinghai Province, China.

The HIV/HA pseudotype virus described herein contains a luciferase gene reporter gene. Upon entering into a target cell, the viral RNA is reverse transcribed, actively imported into the nucleus, and stably integrated into the genome. Luciferase activity in the transduced cells provides a measure of virus infectivity. (Basu et al., J. Virol., 81: 3933-3941 (2007); Manicassamy et al., 2005, supra). The luciferase assay is highly sensitive and is suitable for a 96-well plate format. In addition, the use of non-replicating HIV derived influenza pseudotypes make HTS feasible without the need for stringent biohazard conditions required for handling pathogenic avian influenza strains. Both are key advantages of HIV/HA for developing an HTS assay to measure virus attachment and entry. Several important parameters were optimized in order to isolate the small molecules described herein including: (a) generation of HIV/HA (b) target cells to be used (c) titration of HIV/HA and (d) controls to maximize infectivity and signal to background (S/B) ratio (>100/1).

pNL luc3 R–E– and pNL luc3 R+E– are plasmids based on the HIV-1 proviral clone pNL4-3. These plasmids differ from previous versions in that both plasmids contain Promega's luc+ gene, a third generation firefly luciferase gene optimized for expression in mammalian and plant cells. They can be distinguished from previous versions of the pNL luc plasmids by the presence of a 3 following luc in their respective names.

To construct the pseudotype virus described herein, the envelope-defective proviral genome pNL4.3.LucR–E– containing a luciferase reporter gene was used as the HIV-1 expression vector. (He et al., J. Virol., 69: 6705-6711 (1995)). In the pNL4.3.Luc.R–E– vector, the firefly luciferase gene is inserted into the pNL4-3 nefgene. Two frameshifts (5' Env and Vpr aa 26) render this clone Env– and Vpr– making it competent for only a single round of replication. The vector was licensed from Dr. Ned Landeau from the Salk Institute. To construct the pseudotype virus described herein, the cDNA encoding the HA gene was cloned into the mammalian expression vector pcDNA3 (Invitrogen) under the control of a CMV promoter. To generate an HIV-derived influenza pseudotype expressing HA [HIV/HA], pNL4.3.Luc.R−E−, was co-transfected with the H5 HA(pcDNA3-HA) into 293T cells as previously described. (Basu et al., J. Virol., 81: 3933-3941 (2007); Manicassamy et al., 2005, supra; Cormier et al., Proc. Natl. Acad. Sci. USA, 101: 14067-14072 (2004)). The supernatants containing the pseudotype viruses were collected at 48 h post-transfection, combined, filtered through a 0.45-μm-pore-size filter and assessed for infectivity following standard protocols. (Basu et al., J. Virol., 81: 3933-3941 (2007); Hsu et al., Proc. Natl. Acad. Sci. USA, 100: 7271-7276 (2003); "Production and Use of HIV-1 Luciferase Reporter Viruses", Enna Williams M. Eds. Current Protocols in Pharmacology, 12.5.1-12.5.12, John Wiley & Sons (2004); Connor et al., Virology, 206: 935-944 (1995)).

Figure 3:
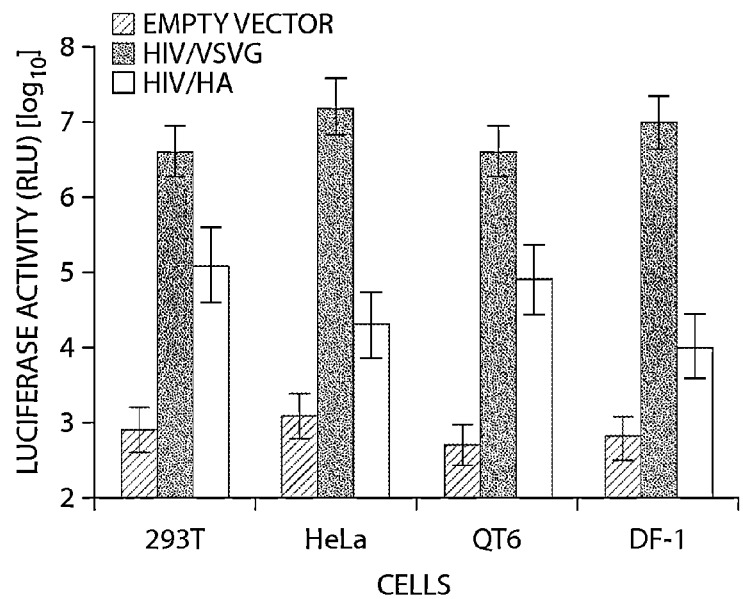
FIG. 3 shows the infectivity (luciferase activity) of HIV/HA pseudotype virus in four cell lines: 292T (human), HeLa (human), QT6 (quail), and DF-1 (chicken) cells as compared with controls. All four cell lines infected with the HIV/HA pseudotype virus displayed high levels of luciferase activity indicating infectivity.

Plasmids encoding VSV-G (HIVNSV-G) and an empty vector were also cotransfected with pNL4.3.Luc.R−E− to generate a control pseudotype virus. The p24 content of pseudotype viruses was measured using a commercially available kit (Beckman Coulter, Calif.) for direct comparison of their respective infectivities. 293T (human), HeLa (human), QT6 (quail), and DF-1 (chicken) cells were infected with p24 normalized HIV/HA or control virions, and the luciferase activities of the cells were determined 48 hours post-challenge (FIG. 3). As expected, all of the four cell lines infected with the VSV-G pseudotype HIV virions displayed high levels of luciferase activity (6.6 to 7.2 logs of RLUs), while the empty vector-infected cells displayed lower levels of luciferase activity (2.8 to 3.1 logs of RLUs). The cells infected by the HIV/HA virions expressed luciferase activity approximately 100-fold higher than background, suggesting that all of these cells, of both human and avian origin, can be infected by the HIV/HA viruses.

These results demonstrate a functional assay to study the entry mechanism for H5N1 infection. It is important to emphasize that this functional assay will greatly alleviate the safety concerns of using live H5N1 viruses for studies of entry mechanism and for screening of entry inhibitors. This functional assay was used to identify potential small molecule inhibitors that prevent the entry of influenza virus into host cells As described below, by employing this assay, it has been demonstrated that human lung cell lines A549 and NCI H661 are highly susceptible to HIV/HA transduction and these cells will be used as the target cells in HTS assay to identify small molecule inhibitors that prevent entry of the HIV/HA into these host cells. In addition, it is important to have an adequate number of target cells/well so that the infected cells will give a good luciferase signal-to-noise background ratio (>100/1).

Example 2

Figure 4:
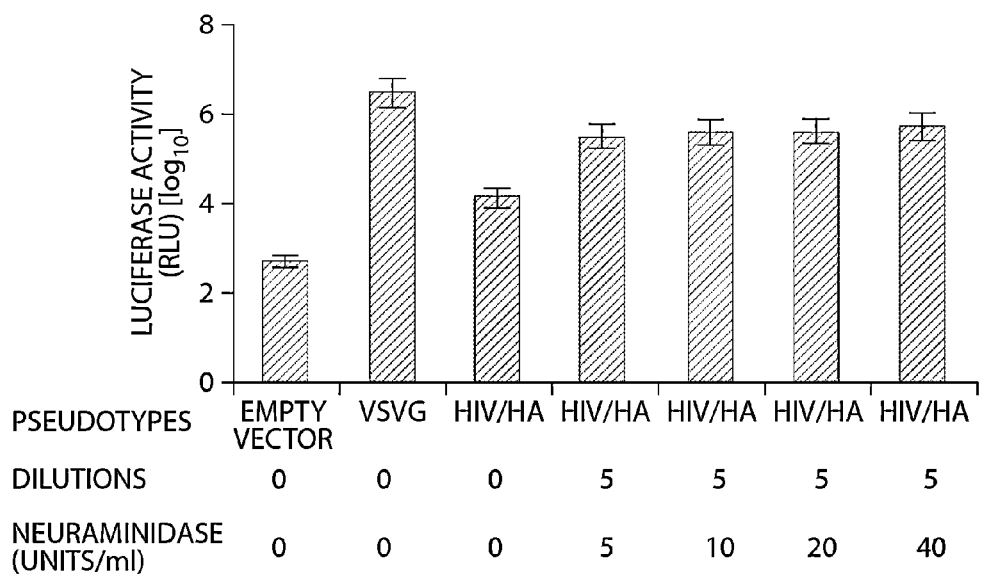
FIG. 4 shows the effect of neuraminidase (NA) treatment (0-40 units/ml) on the infectivity of HIV/HA pseudotype virus in 293T producer cells. Cells treated 26 hr post-transfection with NA (0-40 units/ml) displayed higher levels of infectivity as compared to controls.

Neuraminidase (NA) Treatment of the Producer Cells Enhances Infectivity of the Pseudovirions To optimize the HIV/HA pseudotyping system, neuraminidase (NA) treatment of the 293T producer cells was used to enhance infection of the HIV-based pseudotype viruses. 293T cells were co-transfected with pNL4.3.Luc+R−E− and HA plasmids. Post-transfection (26 h), the transfected 293T cells were treated with NA (New England Biolabs) at concentrations of 0, 5, 10, 20, 40 units/ml. The viral supernatants were diluted 5-fold and used to challenge the target cells. The luciferase activities of the infected cells were determined 48 hours post-infection, and the results are shown in FIG. 4.

Results show that HIV/HA collected from the NA-treated cells displayed at least 10-fold higher luciferase activity than non-treated cells at 5 units/ml NA. Treatment of the producer cells with higher concentrations of NA (10-40 units/ml) further increased the luciferase signals in the target cells, albeit not greatly (5.62 to 5.73 logs). HIV/VSVG and empty vector transfected pseudotype virus were used as controls. These results are consistent with NA treatment facilitating viral release from the producer cells.

In addition, the high signal/background ratio indicates the successful establishment of an efficient HIV/HA pseudotype virus that will be extensively used for the proposed experiments after further HTS optimization.

Figure 10:
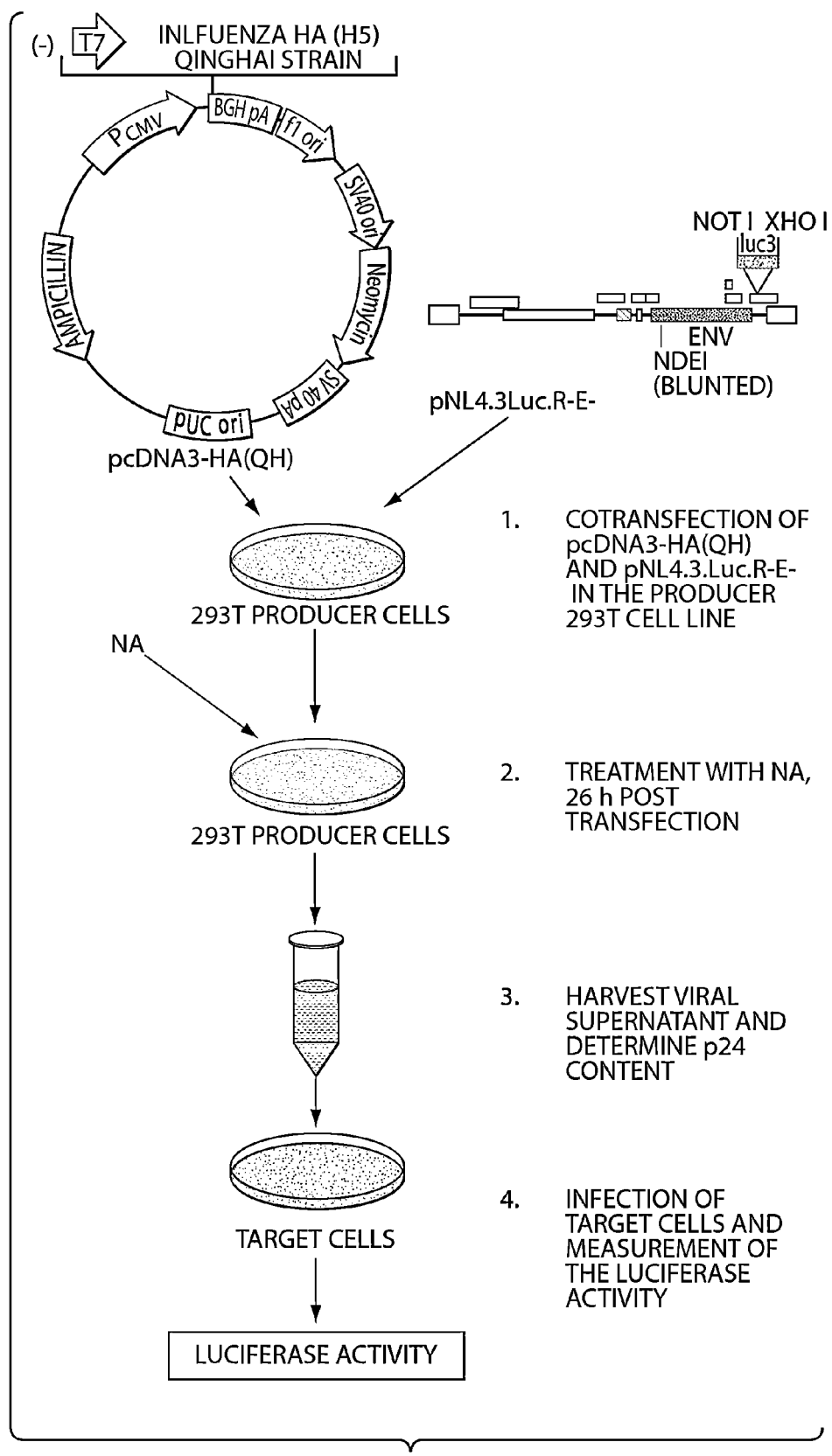
FIG. 10 is a diagrammatic representation of the process for producing the HIV/HA pseudotype virus and infection of cells with the virus.

Therefore, HIV/HA pseudotypes were generated by cotransfection of 293T cells (3×10$^6$ cells in a 100 mm dish, ~70% confluency) with pcDNA3-HA (12 μg) and pNL4.3.Luc.R−E− (12 μg) using lipofectamine 2000 following standard protocol (see FIG. 10). For a control, an HIV derived VSV-G pseudotype (HIVNSV-G) was generated by cotransfection of a plasmid carrying VSV-G, (pcDNA3-VSV-G) and pNL4.3.Luc.R−E− in 293T cells following the same protocol, to establish HA target specificity of the compounds. The HIV/HA or HIV/VSV-G pseudotypes are replication-defective, and the pseudotypes will be evaluated for only one round of the infection process. Virus infectivity is measured from the luciferase activity of the transduced cells. Background activity is determined from luciferase activity of cells infected with supernatants of empty pcDNA3 vector and pNL4.3.Luc.R−E− transfected cells.

Example 3

HIV/HA Pseudotype Virus does not Require Trypsin Treatment

As stated previously, HA cleavage is required for infectivity, because it generates the hydrophobic N-terminus of HA2, which mediates fusion between the viral envelope and the cell membrane. (Skehel et al., 2000, supra; Steinhauer, D. A., 1999, supra; White et al., EMBO J., 1: 217-222 (1982); Luscher-Mattli M., Arch. Virol., 145: 2233-2248 (2000)). The effect of trypsin treatment on the infectivity of HIV/HA derived from H5N1 was investigated. For comparison, another HIV/HA pseudotype virus expressing HA of a low pathogenic avian H5N2 isolate (CK/Michoacan/28159-530/95) was generated. The HA of this strain does not have a cleavage site that can be cleaved by any ubiquitous protease and requires TPCK-treated trypsin treatment for its cleavage. It was kindly provided by Dr. David L. Suarez, USDA.

Figure 5:
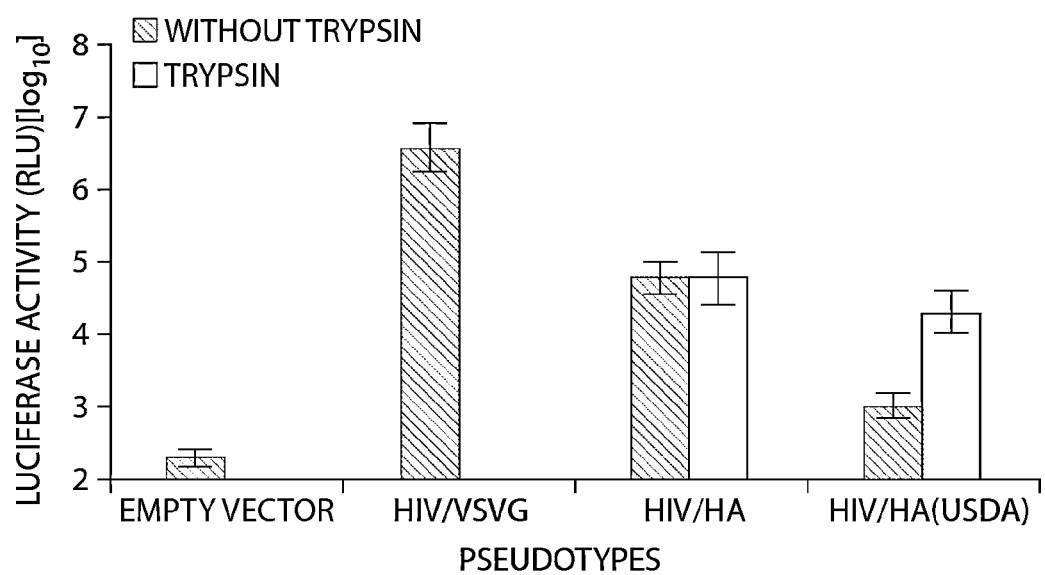
FIG. 5 shows the comparison of HIV/HA and HIV/HA (USDA) pseudotype viruses to infect 293T cells with or without pretreatment with trypsin. Treatment with trypsin did not have any effect on HIV/HA entry as this pseudotype virus includes the protease cleavage site. Pretreatment with trypsin enhanced entry of HIV/HA(USDA) which does not have the natural protease cleavage cite but requires enzymatic treatment for infectivity.

The HIV/HA of this low pathogenic avian isolate is designated as HIV/HA(USDA) to differentiate it from the experimental HIV/HA. HIV/HA or HIV/HA(USDA) pseudotype viruses were either treated with trypsin (50 μg/ml) for 30 min at 37° C. or no trypsin treatment prior to challenging the target 293T cells. Trypsin treatment did not enhance (or inhibit) HIV/HA mediated viral entry (FIG. 5). In contrast, infection of the trypsin-treated HIV/HA(USDA) was greatly enhanced compared to that with no trypsin treatment.

Example 4

Low Pathogenic Laboratory Influenza a Virus [A/WS/33] Requires Trypsin Treatment for Infectivity Influenza A virus laboratory strain A/WS/33 (H1N1) [ATCC #VR-1520] was obtained from American Type Culture Collection. Virus stocks were grown and titrated on MDCK cells. 80% confluent MDCK cells were infected with the virus and allowed to adsorb for 3 h at 37° C., shaking every 15 min to keep the wells covered. Following the incubation, the cells were washed and incubated with EMEM supplemented with 0.125% BSA, 10 mM HEPES (pH 7.4) and with or without 1 μg/ml TPCK-treated trypsin. To determine the effect of trypsin treatment on Influenza A virus [A/WS/33] infectivity, MDCK cells were infected with trypsin treated and untreated influenza A virus strain A/WS/33 at an MOI of 1. As shown in Table 1, there was significant inhibition of infectivity in untreated influenza A virus as compared to the TPCK-trypsin treated viruses. The results are consistent with the HIV/HA(USDA) pseudotype virus results. This further suggests that HA expressed in both the HIV/HA(USDA) pseudotype virus and in low pathogenicity laboratory strains behaves similarly and validates the pseudotype virus model described herein.

TABLE 1

Effects of trypsin treatment

| Cell | Titer (pfu/ml) of influenza A [A/WS/33] virus strain | |
|---|---|---|
| | Trypsin treated | Untreated |
| MDCK | $2.5 \times 10^7$ | $5 \times 10^3$ |
| A549 | $8.6 \times 10^7$ | $2. \times 10^4$ |

Three independent experiments were performed to determine the virus titer.

Example 5

HIV/HA Pseudotype Virus is Sensitive to Lysosomotropic Compounds During

Figure 6A:
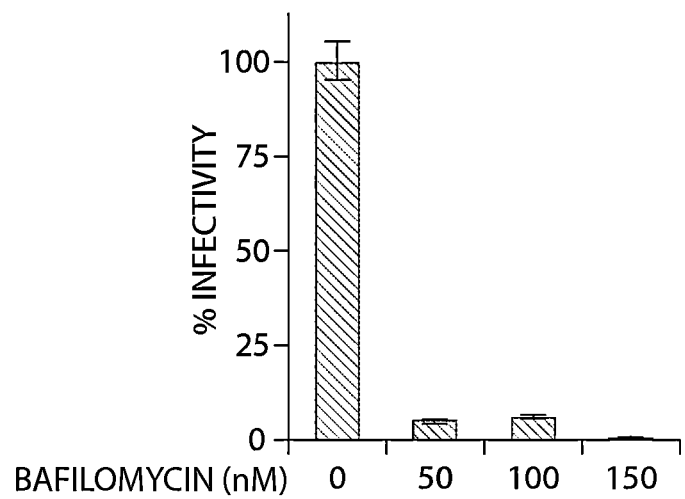
FIG. 6 shows the effect of bafilomycin A (0-150 nM) which blocks acidification of endosomes and $NH_4Cl$ (0-25 nM), a weak base, on the infectivity of HIV/HA pseudotype virus on 293T cells. Pretreatment of 293T cells with bafilomycin prevented HIV/HA infection of the cells indicating entry of HIV/HA into the cell is dependent on a low pH environment.
Figure 6B:
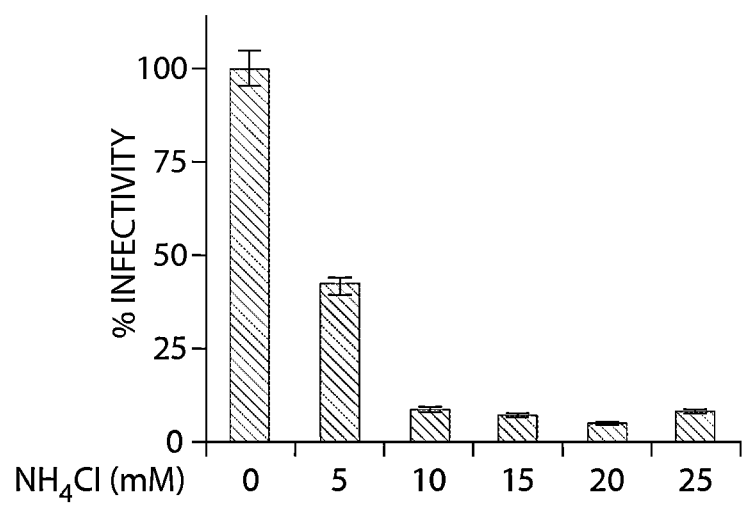

To test the pH-dependence of HA-mediated viral entry, a predetermined titer of HIV/HA was used to infect 293T cells in the presence of bafilomycin A and ammonium chloride ($NH_4Cl$). Bafilomycin A is a highly selective inhibitor of endosomal H+-ATPases which blocks the acidification of endosomes, raising the endosomal pH. (Marsh et al., Adv. Virus Res., 36: 107-151 (1989); Bowman et al., Proc. Natl. Acad. Sci. USA, 85: 7972-7976 (1988); Yoshimori et al., J. Biol. Chem., 266: 17707-17712 (1991); Dröse et al., Biochemistry, 32: 3902-3906 (1993)). Likewise, $NH_4Cl$ is a weak base and raises the endosomal pH. (Marsh, M. 1989, supra). As shown in FIG. 6, panel A, treatment of 293T cells with bafilomycin A efficiently inhibited the infectivity of HIV/HA pseudotype virus between 50-150 nM. Similarly, exposure of cells to the $NH_4Cl$ [5-25 mM] during the first 3 h of virus adsorption significantly reduced the virus infection compared to an untreated control (FIG. 6, panel B). Therefore, the results suggest that HIV/HA entry is dependent on low-pH-induced alterations in HA.

Example 6

Bafilomycin A Inhibits Influenza A Virus [A/WS/33] Infection

The effect of bafilomycin A on influenza A virus infectivity was investigated. MDCK cells (~80% confluent in 6 well plates) were treated for 15 min with serially diluted doses of bafilomycin A (25-200 nM). Influenza A virus (~100 pfu/well) were added to cells, and adsorbed for 3 h at 37° C. Bafilomycin A was also present during the 3 hr adsorption period. Following incubation, the unabsorbed virus was removed by washing, and cells were overlaid with 0.8% agarose containing EMEM supplemented with 4% bovine serum albumin and 1 μg/ml of TPCK-treated trypsin and incubated for 3 days at 37° C. Three independent experiments were performed to determine the virus titer.

Figure 7:
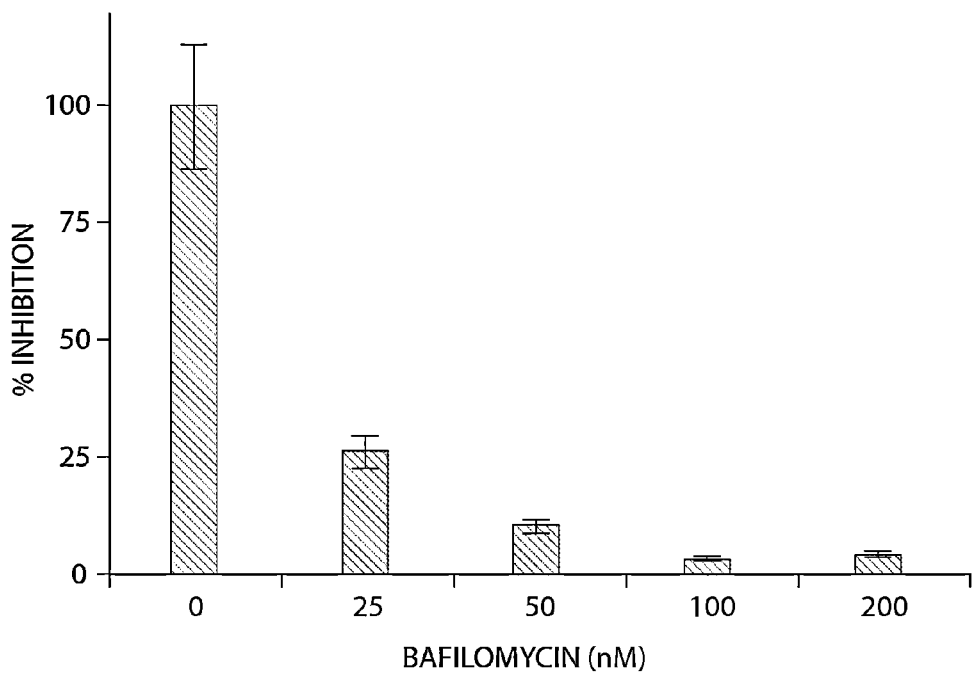
FIG. 7 shows the effect of bafilomycin (0-200 nM) treatment on the infectivity of influenza strain A/WS/33 on MDCK cells. The results suggest that influenza A virus A/WS/33 entry is also dependent on a low pH environment.

As shown in FIG. 7, bafilomycin A efficiently inhibited the infectivity of influenza virus infection at the concentrations tested (25-200 nM). Therefore, the results suggest that the influenza A virus A/WS/33 entry is also dependent on low-pH-induced alterations in HA and validates the HIV/HA pseudotype virus model described herein.

Example 7

Human Lung Cells Display Maximum Infectivity to HIV/HA Pseudotype Virus

Figure 8:
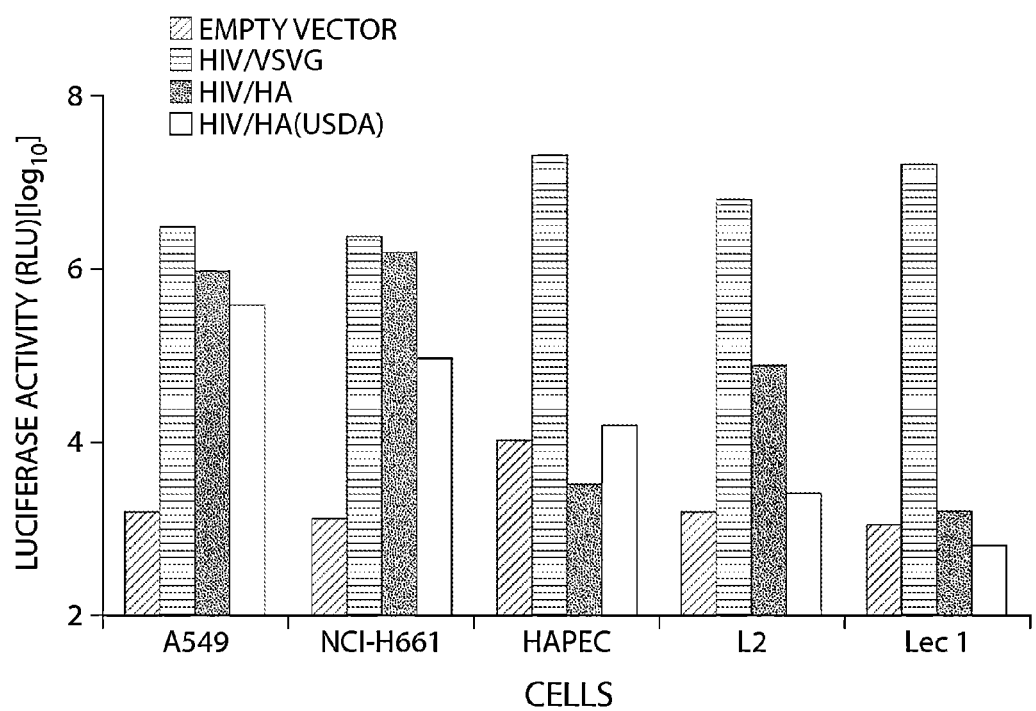
FIG. 8 shows the susceptibility to infection of a number of target cell lines to the HIV/HA pseudotype virus. The human lung cell lines A549 and NCI/H661 were highly susceptible to infection by HIV/HA. These two cell lines were used for screening the compound libraries for small molecule inhibitors that prevent entry of the influenza virus.

To characterize and compare the host tropism, infectivity of HIV/HA was assessed on a panel of target cell lines by plaque assay following previously described methods. Human lung cell lines (A549, NCI-H661 and HAPEC), and rat lung cell line (L2) were used as the target cells for infection. The Lec1 (Chinese hamster ovary) cell line that is resistant to influenza virus infection was also used. Cells were infected with HIV/HA and HIV/HA(USDA) pseudotype viruses following previously described protocols. HIV/VSVG and empty vector transfected pseudotype virus were used as positive and negative controls respectively. The human lung cell lines A549 and NCI-H661 were highly susceptible to infection by HIV/HA pseudotype virus as compared to the human lung cell line HAPEC (FIG. 8). HIV/HA (USDA) pseudotype virus, treated with trypsin, was also very infectious to these cells. However, untreated HIV/HA (USDA) pseudotype virus was not infectious (data not shown). The rat lung cell (L2) was not very susceptible to infection by both HIV/HA and HIV/HA(USDA), while Lec1 cells were highly resistant to both pseudotypes (FIG. 8). These results indicate that HIV/HA and HIV/HA(USDA) display a preferred entry tropism to human lung cells. The human lung cell lines, A549 and NCI-H661, will be used for screening compound libraries for influenza entry inhibitors after further optimization.

These results suggest that HA in HIV/HA pseudotyped virus retains the functional properties of HA present in infectious influenza virus.

Example 8

Development of an HA Binding Assay to Susceptible Cells

Figure 9A:
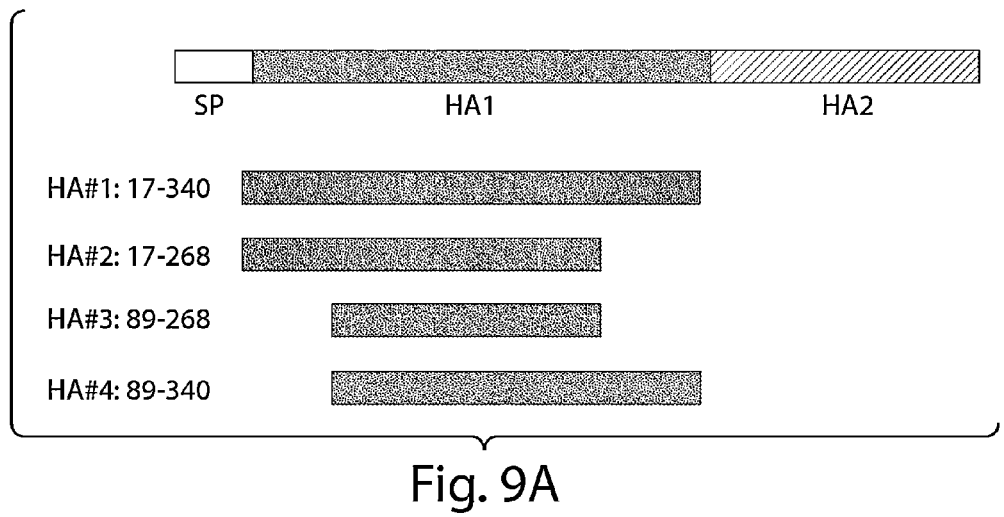
FIG. 9A shows the four different regions of H5N1 HA1 that were fused with human IgG Fc to generate fusion proteins.
Figure 9B:
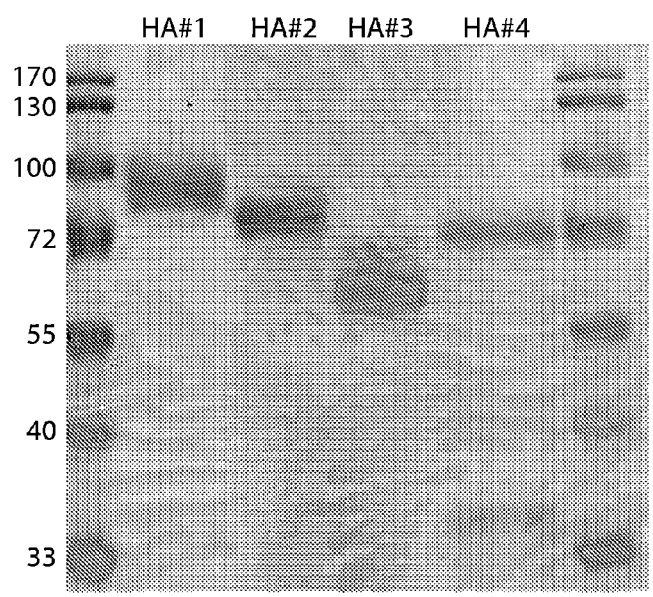
FIG. 9B shows one microgram of each fusion protein run on SDS-PAGE and stained with Coomassie blue.

A HA-binding assay was developed for elucidating the mode of HA/inhibitor interactions. Four different regions of H5N1 HA1 (labeled as #1-4 in FIG. 9A) were fused with human IgG Fc to generate fusion proteins. All of the constructs were confirmed by DNA sequencing. These fusion proteins were expressed and purified according to a protocol of Kuhn et al., J. Biol. Chem., 281: 15951-15958 (2006), with modifications. Briefly, each plasmid was transfected into 293T cells. Cells were replenished with VP-SFM media supplemented with 4 mM L-glutamine for 16 hours post-transfection. Supernatant was collected twice at 48 and 72 hours, and was filtered through a 0.45 μM filter. Each supernatant was applied to protein A agarose (Santa Cruz Biotech) assembled in columns (Pierce). The protein A agarose was washed twice with PBS and proteins were eluted three times with 1 ml 0.1M Glycine (pH 2.8) by centrifugation. The proteins were neutralized immediately after elution by adding 60 µl Tris.HCl (pH8.0). The proteins were then dialyzed in PBS by Slide-A-Lyzer dialysis cassettes (Pierce) and concentrated by Centricon Centrifugal Filter Units (Millipore). One microgram of each purified protein was run on SDS-PAGE followed by Coomassie bright blue staining (FIG. 9B). Depending on the constructs, 0.1-1 mg of fusion protein can be purified by pooling the supernatants from 100 mm plates, which was suitable for the binding assay described below.

Figure 9C:
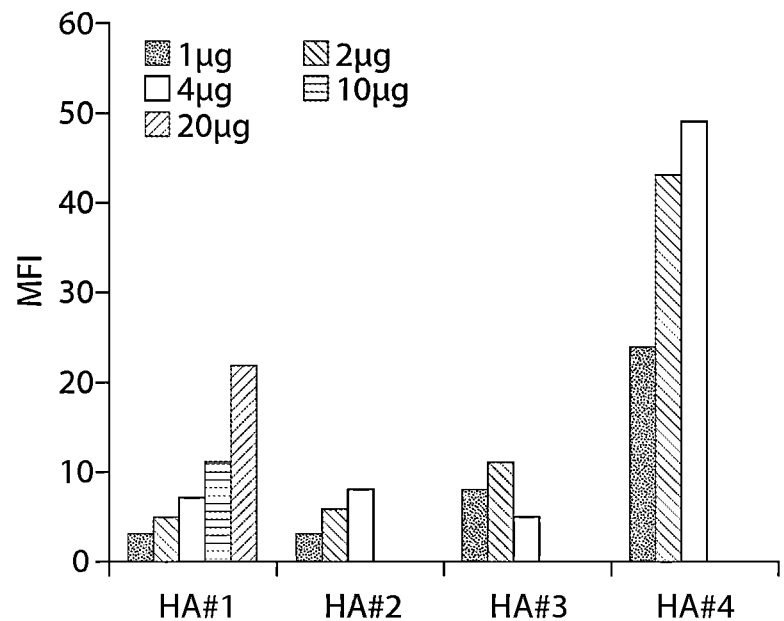
FIG. 9C shows the binding of the fusion proteins (1 µg-20 µg) to 293T cells as measured by flow cytometry. Constructs #2 and #3 did not show good binding but construct #1 and #4 did show good binding to 293T cells. It is interesting that construct #4 which lacks residues 17-88 of the N-terminus of HA1 showed better binding to 293T cells than contruct #1 which is the full-length HA1 protein.

Binding of these proteins to cells was measured using flow cytometry as described by Kuhn et al., 2006, supra). Briefly, 293T cells were detached by PBS/5 mM EDTA and resuspended in PBS/1% BSA and kept on ice for 30 min. Different amounts of HA-hIgG proteins (1 to 20 µg) were incubated with $0.5 \times 10^6$ cells on ice for 1 hour followed by two washes with PBS/1% BSA. Anti-human IgG antibody conjugated with FITC was incubated with cells on ice for 45 minutes at a dilution of 1:100. Cells were washed three times with PBS/1% BSA and twice with PBS and subjected to flow cytometry. Mean fluorescent intensity (MFI) of negative control (no HA-hIgG protein was added) was subtracted from MFI of HA#1 to HA#4 (FIG. 9C). It is clear that Constructs #2 and #3 did not display much binding to 293T cells under these conditions. In contrast, Constructs #1 and #4 displayed a dose-dependent binding to the target cells. It is interesting that Construct #4 has the N-terminal end of HA1 deleted (residues 17-88), but it gave a better binding to the target cells than the full-length HA1 fusion protein (#1).

Figure 9D:
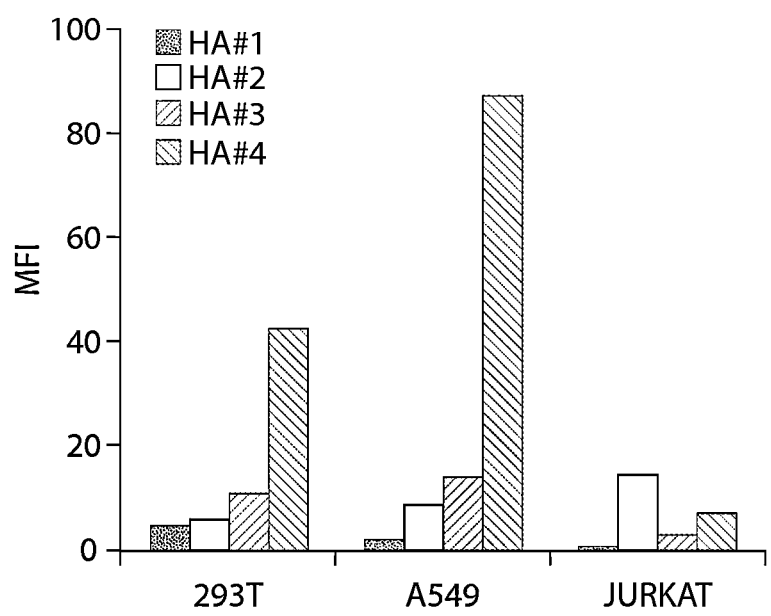
FIG. 9D shows the binding of the fusion proteins to susceptible 293T and A549 cells and resistant Jurkat (human T cell line) cells. As expected, construct #4 showed significant binding to the 293T and A549 cells but not the Jurkat cells. Therefore these results indicate that a sensitive HA binding assay has been developed.

To further characterize the cell binding properties of these fusion proteins, two susceptible and one resistant cell lines were used in the assay. Both 293T and A549, a human lung cell line, have been shown to be highly susceptible, while Jurkat, a human T cell line, is resistant to HIV/HA infection. 2 µg of each fusion protein was used. Under these conditions, only Construct #4 displayed significant binding to the susceptible cells, while the remaining three fusion proteins did not show much binding. Importantly, none of the fusion proteins showed much binding to Jurkat cells (FIG. 9D), consistent with the transduction data presented above. These experiments demonstrate that one of the fusion proteins (Construct #4) can specifically bind to susceptible cells even at 2 µg. This demonstrates the development of a sensitive HA binding assay which will be used in subsequent experiments.

Based on the above examples, it was possible to screen a structurally diverse compound library to identify small molecule inhibitors to prevent entry of influenza virus into host cells and prioritize the chemical hits by using secondary assays. As described above, a HTS assay was developed to identify inhibitors targeting influenza HA during virus entry. By using this assay, it was possible to screen from medium to high throughput assay conditions (>1000 compounds/day), as well as easy readout (luciferase/GFP reporter), and a high signal/background ratio (>10/1).

1. Evaluation of HA Inhibitors Using "Low Pathogenic" H5 Influenza Viruses.

The strict biocontainment measures, required for experiments with live infectious Influenza H5N1 virus, will limit the number of "hits" that can be evaluated against "live" H5N1 virus. Therefore, "hits" will be screened (from above) in a blind fashion against low pathogenic avian influenza A virus strain, CK/Michoacan/28159-530/95 (USDA strain) expressing the H5 subtype of HA (Liu et al., Science, 309: 1206 (2005)) and their potency will be evaluated against live infectious virus in cell culture. This strain was obtained from Dr. David L. Suarez (USDA) and does not require such strict biocontainment as the wild type H5N1 viruses. The only difference between the H5 HA of USDA strain and the wild type H5N1 is the absence of the canonical furin cleavage site (RRRKKR) that can be cleaved by any ubiquitous protease. (Liu et al., Science, 309: 1206 (2005)). Numerous reports have indicated that this polybasic cleavage peptide of the H5 HA protein is required for high pathogenicity of H5 viruses. (Steinhauer, D. A., 1999, supra; Garten, W., 1999, supra); Horimoto, T., 1997, supra; Stieneke-Grober et al., EMBO J., 11: 2407-2414 (1992); Horimoto et al., 1994, supra). Since it is not expected that our "hits" will affect HA cleavage (due to the screening strategy that relies in pseudotyped viruses with already cleaved HA), it is predicted that "hits" that inhibit highly pathogenic H5N1 viruses will also inhibit the USDA strain. The "hits" with the best inhibitory activity against this low pathogenic USDA strain will be further evaluated with wild type H5N1. This final evaluation is necessary because wild type H5N1 viruses are more aggressive than low pathogenic influenza viruses.

Influenza A virus strain, CK/Michoacan/28159-530/95, will be grown in the allantoic cavity often-day-old fertile hen eggs. Briefly, viruses will be injected in the allantoic cavity and incubated for 28-42 h at 37° C. The supernatants will be divided into small aliquots, flash frozen and stored at −80° C. for future use. Each aliquot will be thawed for a single time prior to use. For determining the virus titer, serially-diluted virus suspensions will be inoculated into confluent MDCK monolayer cell cultures in 6-well plates and incubated for 2 h at 37° C. The cells will be washed and overlaid with DMEM containing 0.6% agarose and 2 µg/ml acetylated trypsin, and incubated at 37° C. for 2 days. Plaques will be visualized by giemsa staining. (Anders et al., J. Gen. Virol., 75: 615-622 (1994)).

Inhibition of Influenza Virus Infectivity.

Viruses will be preincubated (1 h) with the serially diluted "hits" at 37° C., and added to MDCK cells ($2 \times 10^5$ cells/ml) in 96 well microtiter plates at a MOI of 0.1 in a total volume of 0.1 ml. Untreated viruses will be used as positive controls. After 2 h incubation at 37° C., unadsorbed virus will be removed by washing and fresh medium containing 2 µg/ml trypsin will be added to the cells and incubated for 2 days at 37° C. Background will be determined in each plate by infecting cells with allantoic fluid from uninfected eggs. As comparators known influenza inhibitors bafilomycin A1, amantadine and stachyflin will be used. (Yoshimoto et al., Arch. Virol., 144: 865-878 (1999)). Following incubation, the culture supernatants will be harvested and the lactate dehydrogenase (LDH) activity of the culture supernatants will be measured. LDH is an oxidative enzyme that changes lactate into pyruvate during glycolysis. LDH widely exists in cell membranes and cytoplasm, and is released from cells into culture supernatants immediately after cell damage. (Decker, T. and M. L. Lohmann-Matthes, J. Immunol. Meth. 115: 61-69 (1988)). Therefore quantitation of the extracellular LDH will provide a measure of virus infectivity. The LDH activity of the supernatant will be measured by CytoTox 96® Non-Radioactive Cytotoxicity Assay kit (Promega Corporation, USA) according to the manufacturer's instructions. The percent inhibition of influenza virus infection will be calculated as (% inhibition)=$100-[\{(OD_T)_V-(OD_C)_M\}/\{(OD_C)_V-(OD_C)_M\}] \times 100$. $(OD_T)_V$ is the absorbance (LDH activity) of the virus-infected culture supernatant in the presence of inhibitors, $(OD_C)_V$ is that of the virus infected culture supernatant in the absence of inhibitors (positive control), $(OD_C)_M$ is that of cells infected with allantoic fluid from uninfected eggs (negative control/background). Inhibitors displaying an $IC_{50}<10$ µM will be picked from stock plates and further confirmed by plaque assay. The percent inhibition will be calculated as =100×[Plaque number in the presence of compound/Plaque number of positive control (without any inhibitor)]. Compounds displaying a positive result ($IC_{50}$<10 μM) ["secondary hits"] will be further examined against recombinant H5N1 strains as described below.

Inhibition of "Live" H5N1 Viruses in Tissue Culture.

Anti-H5N1 influenza activity of the "secondary hits" will be verified against recombinant pandemic H5N1 influenza virus in an enhanced BSL3 containment facility. Recombinant viruses possessing the HA from a highly pathogenic H5N1 Vietnam strain (A/Vietnam/1203/2004) will be generated using the reverse genetics system of Fodor et al., J. Virol., 73: 9679-9682 (1999), and following the methods of Basler et al., Proc. Natl. Acad. Sci. USA, 98: 2746-2751 (2001). The currently circulating pathogenic H5N1 Vietnam strain (A/Vietnam/1203/2004) was chosen because it has characteristics suggestive of a new pandemic strain. The inhibitory activity of the "hits" on the H5N1 strain will be confirmed by a plaque assay using MDCK cells. The percent inhibition will be calculated as =100×[Plaque number in the presence of compound/Plaque number of positive control (without any inhibitor)].

FIG. 11 shows a design workflow diagram for advancing small compound "hits" from the initial screening stage with HIV/HA to an HA specific influenza inhibitor suitable for use as a vaccine in humans and other mammals.

Example 9

Initial Screening of Compound Library to Identify Small Molecule Inhibitors of Influenza Virus As outlined above, pseudotype viruses were produced by co-transfecting 12 μg of construct containing appropriate virus envelope glycoprotein with 12 μg pNL4-3-Luc-R–E–HIV vector into 293T cells (90% confluent) in 10 cm plates with Lipofectamine 2000 (Invitrogen) according to the supplier's protocol. Cell culture grown influenza H1N1 (PR8) viruses were propagated and titrated in MDCK cells over 3 days at 37° C. in the presence of 1 μg/ml tosylsulfonyl phenylalanyl-chloromethylketone (TPCK)-treated trypsin (Sigma-Aldrich) following standard protocol. (Centers for Disease Control and Prevention, 2004, supra).

The chemical libraries screened represent broad and well-balanced collections of over 152,500 compounds. They were purchased from Chembridge (San Diego, Calif.) and Timtec (Newark, Del.), diluted in 96-well master plates at 2.5 mM in dimethyl sulfoxide (DMSO), and stored at −20° C. Compounds were selected in the molecular weight range of 200-500 Da. They have favorable c Log P values (calculated logarithm of n-octanol/water partition coefficient), and encompass over 200 chemotypes.

High throughput screening of combinatorial chemical libraries using pseudotype virus was performed in 96-well plates. Low passage A549 cell monolayers were infected with 100 μL of pseudotype virus containing 8 μg/ml polybrene in the presence of 25 μM (final concentration) test compounds. After 5 h, the inoculum was removed, fresh media was added and the plates were incubated for 72 h at 37° C. and 5% $CO_2$. Infection was quantified using the Britelite Plus™ assay system (Perkin Elmer) in a Wallac EnVision 2102 Multilabel Reader (Perkin Elmer, MA). The percent inhibition was calculated as: 100×[Relative Luciferase Unit (RLU) in the presence of compound−RLU of negative control/RLU of positive control (without any inhibitor)−RLU of negative control].

AlphaScreen SureFire GAPDH Assay Kit (Perkin Elmer) was used to test cell viability by measuring endogenous cellular GAPDH in cell lysates according to manufacturer's protocol.

Results

Approximately 40,000 discrete compounds were screened, and 141 primary hits were identified. The Z' factor for the HTS was 0.5±0.2. Primary hits were counter-screened with pseudotype virus expressing an unrelated glycoprotein (VSV-G) and infectious H1N1 virus for their specificity. They were evaluated for their potency and cytotoxicity with resynthesized compounds. Only 36 of the primary hits specifically inhibited the HA mediated entry process. The final hit rate from the HTS was 0.09%. All the 36 hit compounds exhibited $IC_{90}$ values of ≤25 μM. Structurally, the HA inhibitors can be represented as clusters of ≥2 members each and singletons.

The HA inhibitors identified herein included multiple clusters of chemically related structures, as well as singletons. Of five observed "hits" (see, Table 2), one compound in particular, Compound 2, having a sulfonamide scaffold, demonstrated an $IC_{90}$ of 3.9 μM and, based on this result further structure activity relationship (SAR) studies with a group of sulfonamide analogs were conducted. (See, Table 3.)

TABLE 2

Specificity of influenza HA (H5) hits

| | $IC_{90}$ (μM) | | | | $IC_{50}$ (μM) |
|---|---|---|---|---|---|
| Compound | HIV/HA (H5) | HIV/VSV-G | HIV/HA (H7) | HIV/MLV | Influenza H1N1 (PR8) |
| 1 | 26.5 | >100 | >100 | >100 | 20.2 |
| 2 | 3.9 | >100 | >100 | 99.0 | 5.2 |
| 3 | 22.6 | >100 | 41.6 | 12.1 | 16.0 |
| 4 | 20.6 | >100 | 78.4 | 84.4 | 24.5 |
| 5 | 13.4 | 53.4 | 14.9 | 23.7 | 15.1 |

TABLE 3

SAR of sulfonamide analog anti-influenza inhibitors

| Compound | $R_1$ | $R_2$ | $R_3$ | HIV/HA (H5) $IC_{50}$ (μM) | $CC_{50}$ (μM) |
|---|---|---|---|---|---|
| 6 | 2,4-di-Cl | 4-H | 2-F | 5.3 | >25 |
| 7 | 3-OMe | 4-H | 3,5-di-Cl | 18.5 | 31.5 |
| 8 | 2,5-di-OMe | 4-Me | 4-Cl | >100 | >100 |
| 9 | 3,4-di-Cl | 4-H | 4-H | 20 | 42 |
| 10 | 2,4-di-Cl | 4-H | 4-F | 25 | 50.5 |
| 11 | 4-OMe | 4-H | 2-Me | >100 | >100 |
| 12 | 4-OMe | 4-H | 4-F | >100 | >100 |
| 13 | 4-OMe | 4-H | 2,6-di-OMe | >100 | >100 |
| 14 | 2-OMe | 4-H | 2,3-di-Me | >100 | >100 |
| 15 | 2-Me, 4-Cl | 4-Me | 3-OMe | >100 | 43.4 |
| 16 | 4-Cl | 4-Me | 4-OMe | >100 | >100 |
| 17 | 3-Cl | 4-H | 2,6-di-Me | >100 | >100 |
| 18 | 3-Cl | 4-H | 2,4-di-OMe | >100 | >100 |
| 19 | 3-Cl | 4-H | 2-Cl | >100 | 90.3 |
| 20 | 2-Cl | 4-H | 2,6-di-Me | >100 | >100 |

TABLE 3-continued

SAR of sulfonamide analog anti-influenza inhibitors

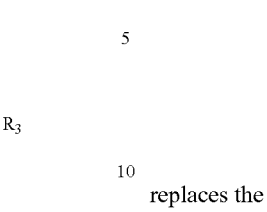

| Compound | $R_1$ | $R_2$ | $R_3$ | HIV/HA (H5) $IC_{50}$ (μM) | $CC_{50}$ (μM) |
|---|---|---|---|---|---|
| 21 | 2-Cl | 4-Me | 2,5-di-OMe | >100 | >100 |
| 22 | 2-Cl | 4-Me | 3-Me | >100 | >100 |
| 23 | 2-Cl | 4-Me | 2,4-di-OMe | >100 | >100 |

Additional substituents investigated for the scaffold shown in Table 3 included ethoxy substituents at $R_1$ (2-ethoxy, 4-ethoxy), halo substituents (F, Cl, Br) at $R_2$, and a flexible linker, e.g., —CH$_2$CH$_2$O—, to replace the direct bond between the $R_3$-substituted phenyl group and the amine nitrogen (that is, a moiety of the formula

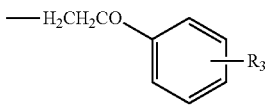

replaces the

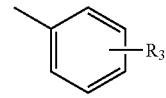

moiety).

The compounds identified above are candidates for development as antiviral agents for the prevention and treatment of influenza infection. The compounds may also be useful as molecular probes for the study of influenza virus entry into host cells.

TABLE 4

Additional validated viral entry inhibitors

| | Compound | | % inhibition @ 25 μM[a] | | |
|---|---|---|---|---|---|
| ID # | Structure | | EBOV[b] | influenza[c] | VSV[d] |
| 30656_D10 | (structure: 2-F phenyl-N(SO2Ph)-CH2-C(O)NH-3-CF3 phenyl) | | 31 | 87 | 59 |
| 30636_C03 | (structure: 4-Me phenyl-N(SO2Ph)-CH2-C(O)NH-2-COOMe phenyl) | | 87 | 26 | 42 |
| 12794_H03 | (structure: 4-MeO phenyl-N(SO2-4-F-phenyl)-CH2-C(O)NH-2-SMe phenyl) | | 100 | 47 | 77 |

TABLE 4-continued

Additional validated viral entry inhibitors

| ID # | Structure | % inhibition @ 25 μM[a] | | |
|---|---|---|---|---|
| | | EBOV[b] | influenza[c] | VSV[d] |
| 12794_B09 | | 100 | 0 | 63 |
| 12838_B07 | | 99 | 46 | 77 |
| 12096_A08 | | 38 | 88 | 42 |
| 12440_F06 | | 93 | 46 | 45 |
| 12441_B08 | | 98 | 33 | 7 |

TABLE 4-continued

Additional validated viral entry inhibitors

| ID # | Structure | % inhibition @ 25 μM[a] | | |
|---|---|---|---|---|
| | | EBOV[b] | influenza[c] | VSV[d] |
| 12305_B04 | | 85 | 47 | 0 |
| 12078_D04 | | 87 | 40 | 60 |
| 12079_A05 | | 86 | 19 | 0 |
| 11978_G07 | | 89 | 22 | 29 |
| 12308_B02 | | 96 | 46 | 23 |
| 12402_E03 | | 85 | 47 | 22 |

TABLE 4-continued

Additional validated viral entry inhibitors

| ID # | Structure | % inhibition @ 25 μM[a] | | |
|---|---|---|---|---|
| | | EBOV[b] | influenza[c] | VSV[d] |
| 11982_F11 | | 25 | 87 | 73 |
| 11997_F05 | | 41 | 100 | 51 |
| 11998_D06 | | 0 | 88 | 0 |
| 12020_E02 | | 43 | 86 | 68 |
| 12076_B09 | | 48 | 86 | 21 |
| 12078_B05 | | 42 | 96 | 36 |

TABLE 4-continued

| Additional validated viral entry inhibitors | | | | |
|---|---|---|---|---|
| Compound | | % inhibition @ 25 μM[a] | | |
| ID # | Structure | EBOV[b] | influenza[c] | VSV[d] |
| 12021_B02 | 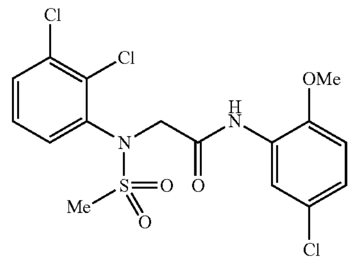 [SMILES: COc1ccc(Cl)cc1NC(=O)CN(c1cccc(Cl)c1Cl)S(C)(=O)=O]  | 0 | 87 | 70 |
| 12066_B08 | 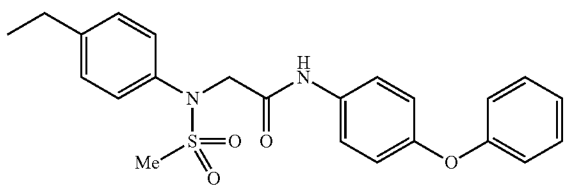 [SMILES: CCc1ccc(N(CC(=O)Nc2ccc(Oc3ccccc3)cc2)S(C)(=O)=O)cc1]  | 31 | 98 | 24 |
| 12112_H02 | 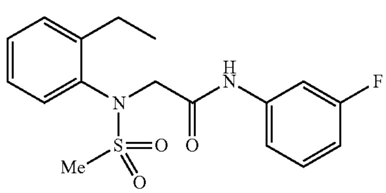 [SMILES: CCc1ccccc1N(CC(=O)Nc1cccc(F)c1)S(C)(=O)=O]  | 0 | 86 | 0 |
| 12110_D02 | 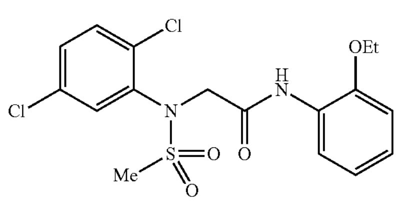 [SMILES: CCOc1ccccc1NC(=O)CN(c1cc(Cl)ccc1Cl)S(C)(=O)=O]  | 0 | 90 | 2 |

[a]Inhibition is expressed as percent inhibition of viral replication with a drug concentration of 25 μM.

[b]Pseudotype ebola virus.

[c]Pseudotype influenza H5N1.

[d]Pseudotype vesicular stomatitis virus.

Example 10

Synthesis Schemes

Scheme 1 Synthesis of aminoacetamide sulfonamide viral inhibitor compound

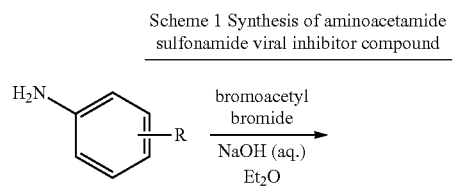

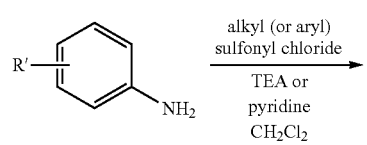

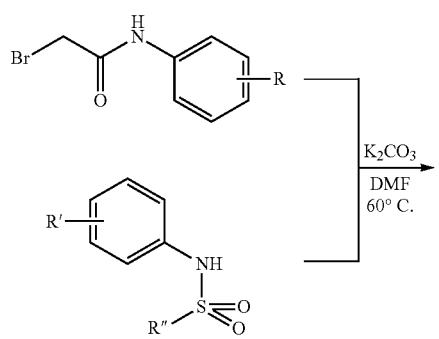

Aminoacetamide sulfonamides are synthesized in a convergent, three-step process beginning from two substituted anilines (which can be the same or different), a sulfonyl chloride, and bromoacetyl bromide. One aniline is acylated by bromoacetyl chloride in the presence of aqueous base to form a bromoacetanlilde, while the other aniline is sulfonylated with a sulfonyl chloride to form a sulfonamide. The sulfonamide is deprotonated with mild base and the resulting anion is used to displace the bromo substituent of the bromoacetanilide to form the target compounds.

Variations in the target compounds are accomplished, generally, at the level of the starting anilines. The substituents R and R' are found in the starting anilines and carried through the synthesis. The substituent R" is found in the starting sulfonyl chloride, and is also carried through the synthesis.

Scheme 2 Representative procedures for the synthesis of aminoacetamide sulfonamides

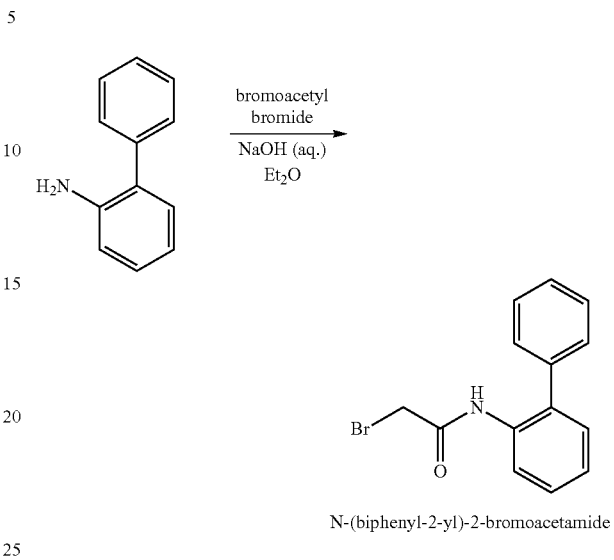

N-(biphenyl-2-yl)-2-bromoacetamide

To a solution of 2-aminobiphenyl (10 g, 59 mmol) in diethyl ether (60 mL) at −10° C. was added 1.0 M aqueous NaOH (32 mL, 32 mmol). A solution of bromoacetyl bromide (11.93 g, 59 mmol) in diethyl ether (30 mL) was added over 15 min. The cooling bath was removed, and the reaction mixture was stirred for an additional 15 min. The mixture was separated, and the aqueous layer was washed with diethyl ether (100 mL). The combined organic extracts were washed with water (2×50 mL) and brine (50 mL), then dried over $MgSO_4$, filtered, and evaporated to one fourth of the original volume. The resulting solids were collected by filtration and dried under high vacuum to provide 6.5 g (37%) of the desired product as a white crystalline solid: $^1$H-NMR (CDCl$_3$) δ 8.32 (d, 2H), 7.53-7.36 (m, 6H), 7.27-7.22 (m, 2H).

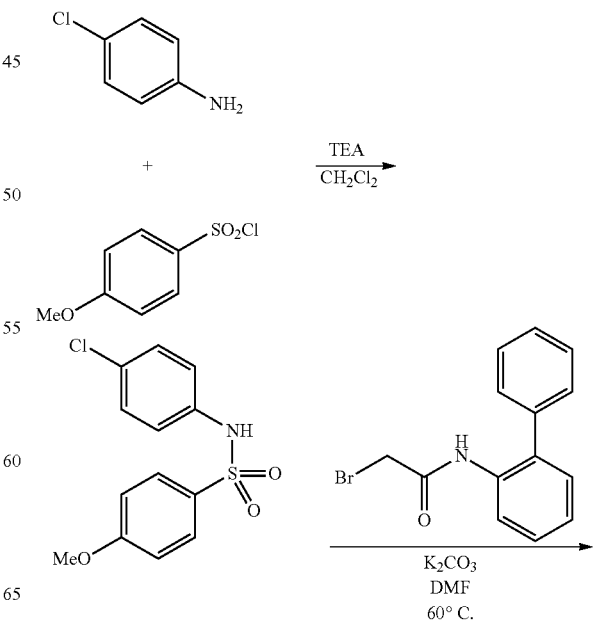

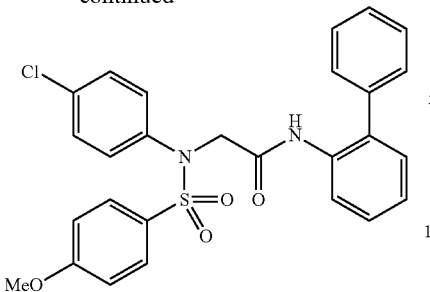

I. N-(4-chlorophenyl)-4-methoxybenzenesulfonamide

To a solution of 4-methoxybenzenesulfonyl chloride (5.0 g, 24 mmol) and 4-chloroaniline (3.1 g, 24 mmol) in dichloromethane (24 mL) at 0° C. was added triethylamine (3.4 mL, 24 mmol) over 10 minutes. The ice bath was removed, and the mixture was stirred for 16 hr. The mixture was diluted with dichloromethane (100 mL) and the combined solution was washed with water (50 mL) and brine (50 mL). The organic solution was dried over $MgSO_4$, filtered, and evaporated, and the crude product was purified by silica gel chromatography (15-60% EtOAc/Hex). Product-containing fractions were pooled, evaporated, and dried under high vacuum to yield 4.9 g (69%) of the product as a tan-colored oil: $^1$H-NMR ($CDC_3$) δ 10.17 (s, 1H), 7.71 (d, 2H), 7.61 (d, 2H), 7.04 (d, 2H), 6.96 (d, 2H), 2.19 (s, 3H).

II. N-(biphenyl-2-yl)-2-(N-(4-chlorophenyl)-4-methoxyphenylsulfonamido)acetamide To a mixture of N-(biphenyl-2-yl)-2-bromoacetamide (150 mg, 0.52 mmol) and N-(4-chlorophenyl)-4-methoxybenzenesulfonamide (154 mg, 0.52 mmol) in DMF (1.5 mL) was added $K_2CO_3$ (180 mg, 1.3 mmol). The resultant suspension was heated to 60° C., for 45 min. The reaction mixture was poured into water (30 mL) and extracted with ethyl acetate (2×50 mL). The combined organic layers were washed with brine (1×50 mL), dried over $Na_2SO_4$, and purified by silica gel chromatography (15-40% EtOAc/Hex). Product-containing fractions were pooled and evaporated to yield 175 mg (66%) of product as a white micro-crystalline solid: mp 100-104° C., $R_f$ 0.17 (25% EtOAc/Hex); $^1$H-NMR ($CDCl_3$) δ 8.78 (s, 1H), 8.49 (d, 1H), 7.72-7.67 (dd, 2H), 7.63-7.60 (m, 1H), 7.50 (d, 2H), 7.42 (d, 2H), 7.36-7.29 (t, 2H), 7.21-7.18 (m, 2H), 7.09-7.04 (t, 1H), 6.94-6.91 (dd, 2H), 6.43 (s, 1H), 6.28 (d, 1H), 4.10 (s, 2H), 3.87 (s, 3H).

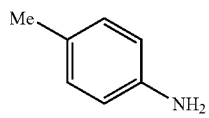

+

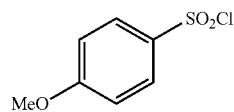

→ TEA / $CH_2Cl_2$

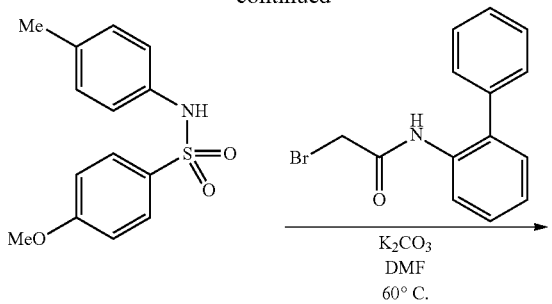

III. N-(4-toluoyl)-4-methoxybenzenesulfonamide

To a solution of 4-methoxybenzenesulfonyl chloride (5.0 g, 24 mmol) and 4-methylaniline (2.6 g, 24 mmol) in dichloromethane (24 mL) at 0° C. was added triethylamine (3.4 mL, 24 mmol) over 10 minutes. The ice bath was removed, and the mixture was stirred for 16 hr. The mixture was diluted with dichloromethane (100 mL) and the combined solution was washed with water (50 mL) and brine (50 mL). The organic solution was dried over $MgSO_4$, filtered, and evaporated, and the crude product was purified by silica gel chromatography (15-60% EtOAc/Hex). Product-containing fractions were pooled, evaporated, and dried under high vacuum to yield 6.4 g (93%) of the product as a tan-colored oil: $^1$H-NMR (DMSO-$d_6$) δ 9.94 (s, 1H), 7.66-7.63 (m, 2H), 7.04-6.93 (m, 6H), 3.77 (s, 3H), 2.16 (s, 3H).

IV. N-(biphenyl-2-yl)-2-(N-(4-toluoyl)-4-methoxyphenylsulfonamido)acetamide

To a mixture of N-(biphenyl-2-yl)-2-bromoacetamide (150 mg, 0.52 mmol) and N-(4-toluoyl)-4-methoxybenzenesulfonamide (144 mg, 0.52 mmol) in DMF (1.5 mL) was added $K_2CO_3$ (180 mg, 1.3 mmol). The resultant suspension was heated to 60° C., for 45 min. The reaction mixture was poured into water (30 mL) and extracted with ethyl acetate (2×50 mL). The combined organic layers were washed with brine (1×50 mL), dried over $Na_2SO_4$, and purified by silica gel chromatography (15-40% EtOAc/Hex). Product-containing fractions were pooled and evaporated to yield 122 mg (48%) of product as a white micro-crystalline solid: mp 160-161° C., $R_f$ 0.19 (25% EtOAc/Hex); $^1$H-NMR (DMSO-$d_6$) δ 9.19 (s, 1H), 7.67 (d, 1H), 7.50 (d, 2H), 7.42 (t, 3H), 7.33-7.24 (m, 5H), 7.07 (d, 4H), 6.75 (d, 2H), 4.24 (s, 2H), 3.83 (s, 3H), 2.27 (s, 3H).

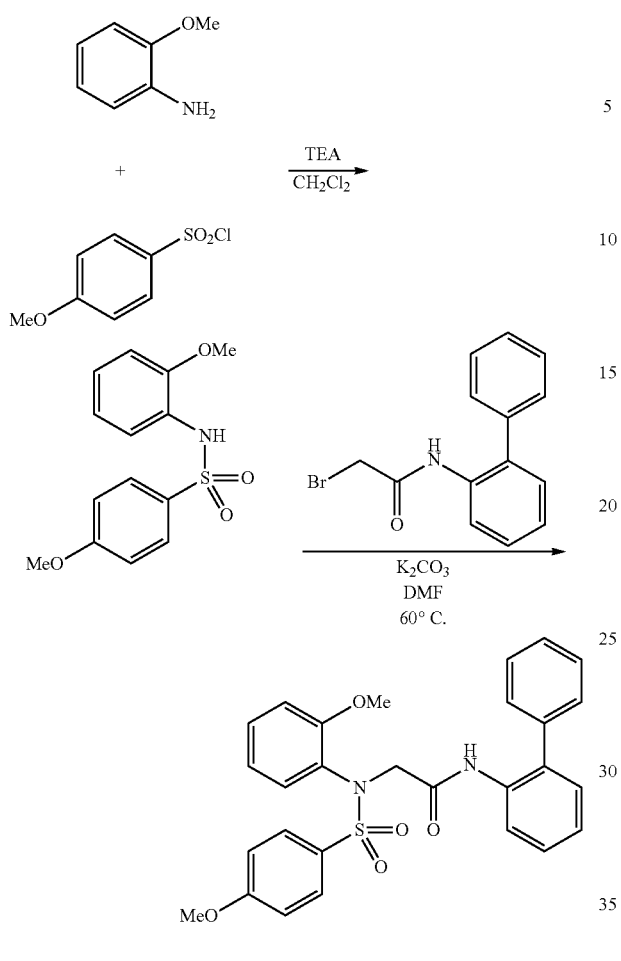

V.
N-(2-methoxyphenyl)-4-methoxybenzenesulfonamide

To a solution of 4-methoxybenzenesulfonyl chloride (5.0 g, 24 mmol) and 2-methoxyaniline (3.0 g, 24 mmol) in dichloromethane (24 mL) at 0° C. was added triethylamine (3.4 mL, 24 mmol) over 10 minutes. The ice bath was removed, and the mixture was stirred for 16 hr. The mixture was diluted with dichloromethane (100 mL) and the combined solution was washed with water (50 mL) and brine (50 mL). The organic solution was dried over MgSO$_4$, filtered, and evaporated, and the crude product was purified by silica gel chromatography (15-60% EtOAc/Hex). Product-containing fractions were pooled, evaporated, and dried under high vacuum to yield 5.3 g (44%) of the product as a tan-colored oil: $^1$H-NMR (CDCl$_3$) δ 7.70-7.67 (d, 2H), 7.53-7.50 (d, 1H), 7.05-6.99 (m, 2H), 6.91-6.83 (m, 3H), 6.73 (d, 1H), 3.80 (s, 3H), 3.65 (s, 3H).

VI. N-(biphenyl-2-yl)-2-(N-(2-methoxyphenyl)-4-methoxyyphenylsulfonamido)acetamide To a mixture of N-(biphenyl-2-yl)-2-bromoacetamide (150 mg, 0.52 mmol) and N-(2-methoxyphenyl)-4-methoxybenzenesulfonamide (153 mg, 0.52 mmol) in DMF (1.5 mL) was added K$_2$CO$_3$ (180 mg, 1.3 mmol). The resultant suspension was heated to 60° C., for 45 min. The reaction mixture was poured into water (30 mL) and extracted with ethyl acetate (2×50 mL). The combined organic layers were washed with brine (1×50 mL), dried over Na$_2$SO$_4$, and purified by silica gel chromatography (15-40% EtOAc/Hex). Product-containing fractions were pooled and evaporated to yield 84 mg (33%) of product as a white micro-crystalline solid: mp 130-131° C., R$_f$ 0.10 (25% EtOAc/Hex); $^1$H-NMR (DMSO-d$_6$) δ 9.16 (s, 1H), 7.68 (d, 1H), 7.51 (d, 2H), 7.40-7.28 (m, 9H), 7.07 (d, 2H), 6.95 (d, 1H), 6.86 (d, 2H), 4.19 (s, 2H), 3.84 (s, 3H), 3.31 (s, 3H).

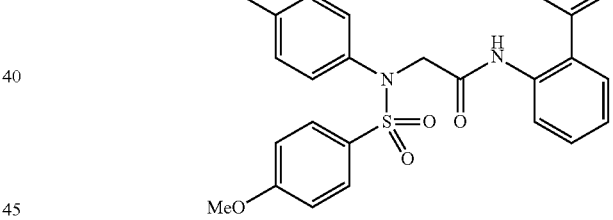

VII.
N-(4-methoxyphenyl)-4-methoxybenzenesulfonamide

To a solution of 4-methoxybenzenesulfonyl chloride (5.0 g, 24 mmol) and 4-methoxyaniline (3.0 g, 24 mmol) in dichloromethane (24 mL) at 0° C. was added triethylamine (3.4 mL, 24 mmol) over 10 minutes. The ice bath was removed, and the mixture was stirred for 16 hr. The mixture was diluted with dichloromethane (100 mL) and the combined solution was washed with water (50 mL) and brine (50 mL). The organic solution was dried over MgSO$_4$, filtered, and evaporated, and the crude product was purified by silica gel chromatography (15-60% EtOAc/Hex). Product-containing fractions were pooled, evaporated, and dried under high vacuum to yield 9.5 g (79%) of the product as a tan-colored oil: $^1$H-NMR (DMSO-d$_6$) δ 9.29 (s, 1H), 7.63 (d, 2H), 7.23-7.19 (m, 1H), 7.11-7.01 (m, 3H), 6.91-6.83 (m, 2H), 3.79 (s, 3H), 3.52 (s, 3H).

VIII. N-(biphenyl-2-yl)-2-(N-(4-methoxyphenyl)-4-methoxyphenylsulfonamido)acetamide To a mixture of N-(biphenyl-2-yl)-2-bromoacetamide (150 mg, 0.52 mmol) and N-(4-methoxyphenyl)-4-methoxybenzenesulfonamide (153 mg, 0.52 mmol) in DMF (1.5 mL) was added $K_2CO_3$ (180 mg, 1.3 mmol). The resultant suspension was heated to 60° C., for 45 min. The reaction mixture was poured into water (30 mL) and extracted with ethyl acetate (2×50 mL). The combined organic layers were washed with brine (1×50 mL), dried over $Na_2SO_4$, and purified by silica gel chromatography (15-40% EtOAc/Hex). Product-containing fractions were pooled and evaporated to yield 112 mg (42%) of product as a white micro-crystalline solid: mp 131-133° C., $R_f$ 0.12 (25% EtOAc/Hex); $^1$H-NMR (CDCl$_3$) 8.98 (s, 1H), 8.35 (d, 1H), 7.62-7.47 (m, 7H), 7.29-7.19 (m, 4H), 6.88 (dd, 2H), 6.71-6.67 (m, 2H), 6.21-6.18 (dd, 1H), 4.20 (s, 2H), 3.85 (s, 3H), 3.22 (s, 3H).

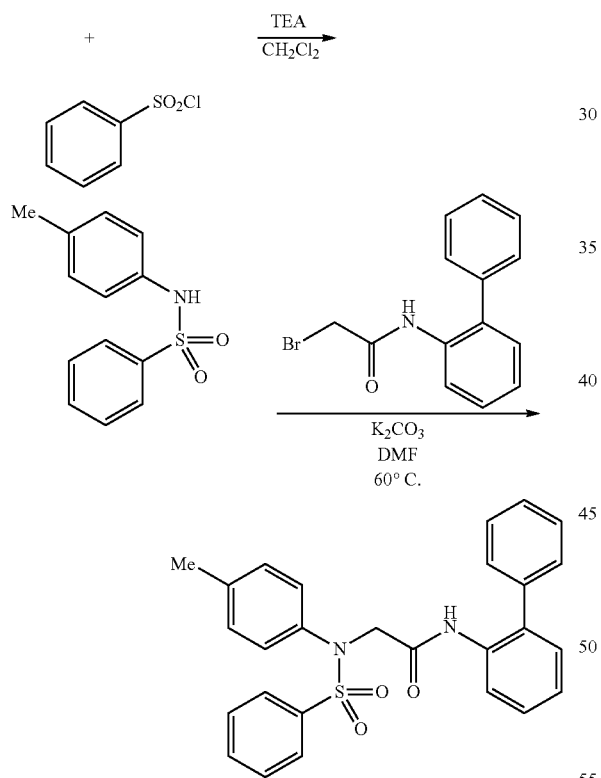

IX. N-(4-toluoyl)benzenesulfonamide

To a solution of benzenesulfonyl chloride (4.2 g, 24 mmol) and 4-methylaniline (2.6 g, 24 mmol) in dichloromethane (24 mL) at 0° C. was added triethylamine (3.4 mL, 24 mmol) over 10 minutes. The ice bath was removed, and the mixture was stirred for 16 hr. The mixture was diluted with dichloromethane (100 mL) and the combined solution was washed with water (50 mL) and brine (50 mL). The organic solution was dried over $MgSO_4$, filtered, and evaporated, and the crude product was purified by silica gel chromatography (15-60% EtOAc/Hex). Product-containing fractions were pooled, evaporated, and dried under high vacuum to yield 10.6 g (97%) of the product as a tan-colored oil: $^1$H-NMR (DMSO-d$_6$) δ 10.09 (s, 1H), 7.73-7.70 (m, 2H), 7.59-7.49 (m, 3H), 6.98 (dd, 4H), 2.17 (s, 3H).

X. N-(biphenyl-2-yl)-2-(N-(toluoyl)phenylsulfonamido)acetamide

To a mixture of N-(biphenyl-2-yl)-2-bromoacetamide (150 mg, 0.52 mmol) and N-(4-toluoyl)benzenesulfonamide (129 mg, 0.52 mmol) in DMF (1.5 mL) was added $K_2CO_3$ (180 mg, 1.3 mmol). The resultant suspension was heated to 60° C., for 45 min. The reaction mixture was poured into water (30 mL) and extracted with ethyl acetate (2×50 mL). The combined organic layers were washed with brine (1×50 mL), dried over $Na_2SO_4$, and purified by silica gel chromatography (15-40% EtOAc/Hex). Product-containing fractions were pooled and evaporated to yield 71 mg (31%) of product as an off-white powder: mp 98-100° C., $R_f$ 0.27 (25% EtOAc/Hex); $^1$H-NMR (CDCl$_3$) 8.84 (s, 1H), 8.48 (d, 1H), 7.72-7.67 (m, 2H), 7.62-7.59 (m, 2H), 7.54-7.46 (m, 6H), 7.46-7.28 (m, 2H), 7.2-7.17 (m, 1H), 6.90 (d, 2H), 6.18 (m, 2H), 4.16 (s, 2H), 2.26 (s, 3H).

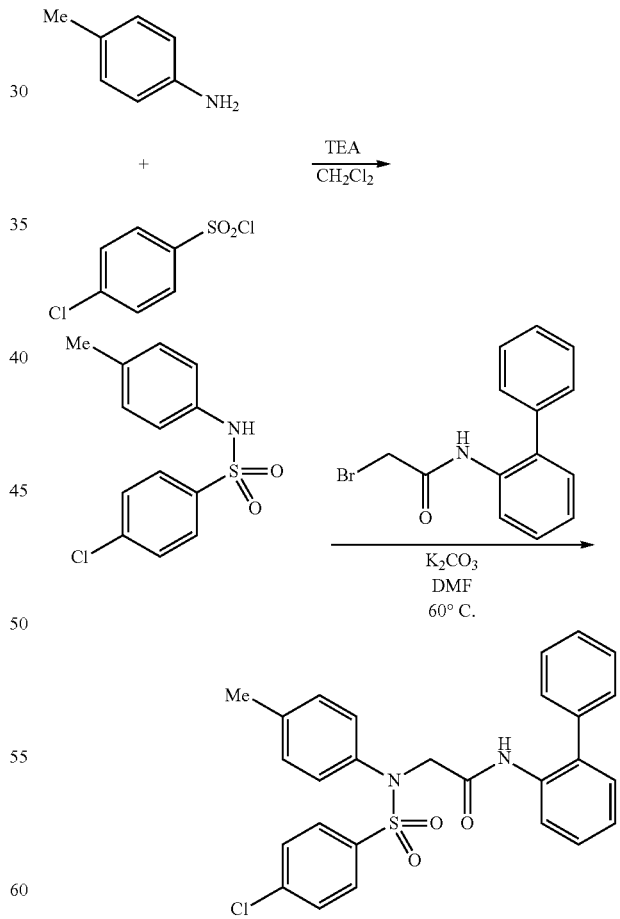

XI. N-(4-toluoyl)-4-chlorobenzenesulfonamide

To a solution of 4-chlorobenzenesulfonyl chloride (5.1 g, 24 mmol) and 4-methylaniline (2.6 g, 24 mmol) in dichloromethane (24 mL) at 0° C. was added triethylamine (3.4 mL, 24 mmol) over 10 minutes. The ice bath was removed, and the mixture was stirred for 16 hr. The mixture was diluted with dichloromethane (100 mL) and the combined solution was washed with water (50 mL) and brine (50 mL). The organic solution was dried over MgSO$_4$, filtered, and evaporated, and the crude product was purified by silica gel chromatography (15-60% EtOAc/Hex). Product-containing fractions were pooled, evaporated, and dried under high vacuum to yield 6.8 g (69%) of the product as a tan-colored oil: $^1$H-NMR (CDCl$_3$) δ 10.17 (s, 1H), 7.71 (d, 2H), 7.61 (d, 2H), 7.04 (d, 2H), 6.96 (d, 2H), 2.19 (s, 3H).

XII. N-(biphenyl-2-yl)-2-(N-(4-toluoyl)-4-chlorophenylsulfonamido)acetamide

To a mixture of N-(biphenyl-2-yl)-2-bromoacetamide (150 mg, 0.52 mmol) and N-(4-toluoyl)-4-chlorobenzenesulfonamide (153 mg, 0.52 mmol) in DMF (1.5 mL) was added K$_2$CO$_3$ (180 mg, 1.3 mmol). The resultant suspension was heated to 60° C., for 45 min. The reaction mixture was poured into water (30 mL) and extracted with ethyl acetate (2×50 mL). The combined organic layers were washed with brine (1×50 mL), dried over Na$_2$SO$_4$, and purified by silica gel chromatography (15-40% EtOAc/Hex). Product-containing fractions were pooled and evaporated to yield 94 mg (37%) of product as a white micro-crystalline solid: mp 159-177° C., R$_f$ 0.42 (25% EtOAc/Hex); $^1$H-NMR (CDCl$_3$) δ 8.77 (s, 1H), 8.48 (d, 1H), 7.71-7.59 (m, 2H), 7.52-7.40 (m, 6H), 7.38-7.32 (m, 1H), 7.29-7.26 (m, 2H), 7.19-7.15 (t, 2H), 6.95-6.23 (m, 2H), 4.13 (s, 2H), 2.27 (s, 3H).

All publications, patent applications, patents, and other documents cited herein are incorporated by reference in their entirety. In case of conflict, the present specification, including definitions, will control. In addition, the materials, methods, and examples are illustrative only and not intended to be limiting.

Obvious variations to the disclosed compounds and alternative embodiments of the invention will be apparent to those skilled in the art in view of the foregoing disclosure. All such obvious variants and alternatives are considered to be within the scope of the invention as described herein.

The invention claimed is:

1. A method of inhibiting influenza virus infection in a mammal comprising administering an effective amount of at least one compound having the structure comprising Formula I:

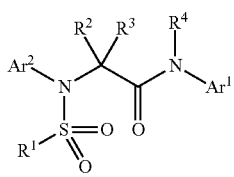

Formula I wherein:
Ar$^1$ and Ar$^2$ are independently an aryl or heteroaryl moiety which may be unsubstituted or substituted by up to 5 substituents selected from the group consisting of halo, amino, amidino, guanidino, alkyl, haloalkyl, alkenyl, alkynyl, cycloalkyl, heterocycloalkyl, aryl, heteroaryl, hydroxy, alkoxy, aryloxy, heteroaryloxy, acyl, carboxy, alkoxycarbonyl, aryloxycarbonyl, alkylamino, acylamino, amido, mercapto, alkylthio, arylthio, hydroxamate, thioacyl, and alkylsulfonyl;

R$^1$ is an alkyl, haloalkyl, alkenyl, alkynyl, cycloalkyl, heterocycloalkyl, aryl, or heteroaryl moiety that may be unsubstituted or additionally substituted by any of the following substituents selected from the group consisting of cycloalkyl, heterocycloalkyl, aryl, heteroaryl, hydroxy, alkoxy, aryloxy, heteroaryloxy, acyl, carboxy, alkoxycarbonyl, aryloxycarbonyl, amino, alkylamino, acylamino, amido, sulfonamido, mercapto, alkylthio, arylthio, hydroxamate, thioacyl, alkylsulfonyl, and aminosulfonyl;

R$^2$ and R$^3$ are independently selected from the group consisting of hydrogen, an alkyl, haloalkyl, alkenyl, alkynyl, cycloalkyl, heterocycloalkyl, hydroxy, alkoxy, amino, alkylamino, and acylamino moiety;

R$^4$ is selected from the group consisting of hydrogen, a monovalent alkyl, haloalkyl, alkenyl, alkynyl, cycloalkyl, and heterocycloalkyl moiety;

and wherein
R$^2$ and R$^3$ may be joined to form carbocyclic or heterocyclic rings; and where R$^2$ and R$^3$ are different, the enantiomer may be of either the (R)- or (S)-configuration, or a racemic compound;

and a pharmaceutically acceptable carrier or excipient.

2. The method according to claim 1, wherein said compound if effective to inhibit influenza virus entry into a host cell.

3. The method according to claim 1, wherein said pharmaceutically acceptable carrier or excipient is selected from binding agents, fillers, lubricants, disintegrants, wetting agents, suspending agents, emulsifying agents, non-aqueous vehicles, and preservatives.

4. The method according to claim 1, wherein said influenza is avian influenza.

5. The method according to claim 4, wherein said avian influenza is the H5N1 subtype.

6. The method according to claim 1, wherein said mammal is a human.

7. The method according to claim 1, wherein said compound is administered via a route selected from intradermally, transdermally, intramuscularly, intraperitoneally, intravenously, or orally.

8. The method according to claim 7, wherein said compound is administered orally.

9. The method of claim 8, wherein said oral administration is selected from the group consisting of a tablet, gelatin capsule, microcapsule, and liquid formula.

10. The method according to claim 1, wherein said compound is selected from the group consisting of:

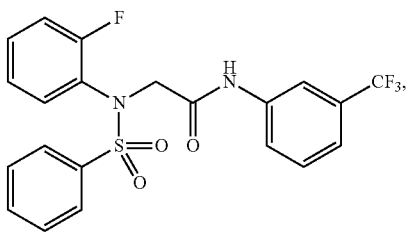

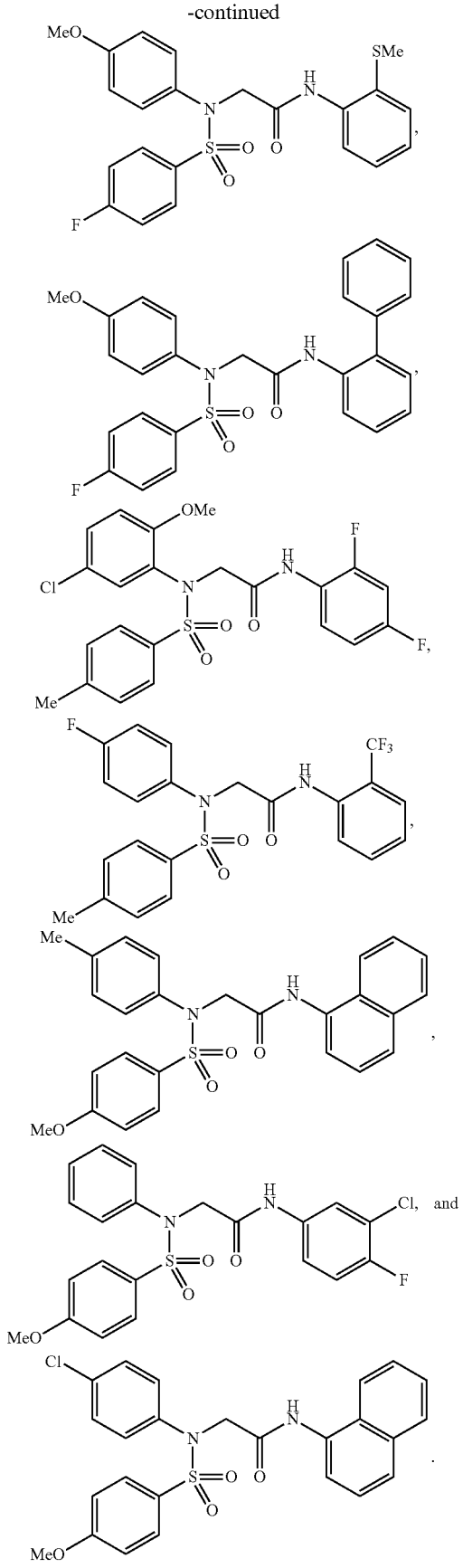
11. The method according to claim 1, wherein said compound is selected from the group consisting of:
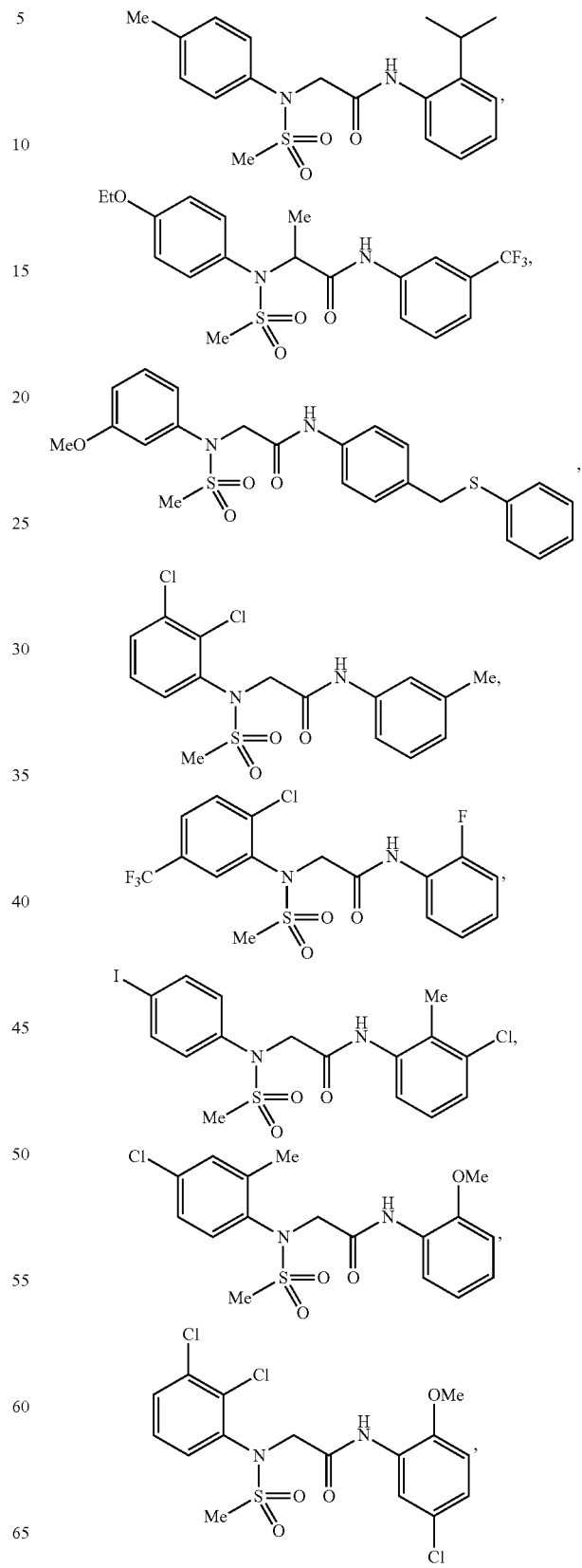

-continued
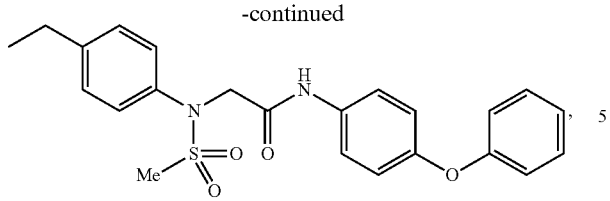
,
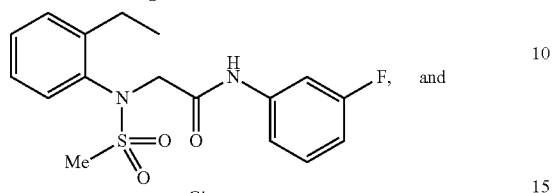
and
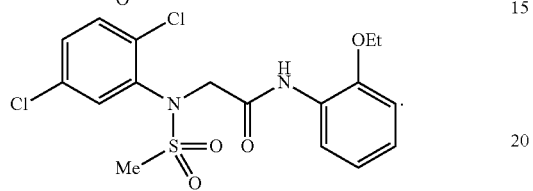
.
* * * * *

UNITED STATES PATENT AND TRADEMARK OFFICE
CERTIFICATE OF CORRECTION

PATENT NO.         : 9,212,134 B2
APPLICATION NO.    : 13/821682
DATED              : December 15, 2015
INVENTOR(S)        : Arnab Basu et al.

Page 1 of 1

It is certified that error appears in the above-identified patent and that said Letters Patent is hereby corrected as shown below:

In The Claims

Claim 2, column 46, line 29, cancel the text beginning with:

"2. A method according to" to and ending "virus entry into a host cell." in column 46, line 31, and insert the following claim:

--2. A method according to claim 1, wherein said compound is effective to inhibit influenza virus entry into a host cell.--

Signed and Sealed this
Fifteenth Day of March, 2016

Michelle K. Lee
*Director of the United States Patent and Trademark Office*